United States Patent [19]

Zimmermann

[11] Patent Number: 4,853,393
[45] Date of Patent: Aug. 1, 1989

[54] 3,5-DIACYL-4-ARYL-1,4 DIHYDROPYRIDINE DERIVATIVES, THEIR USES AND COMPOSITIONS

[75] Inventor: Markus Zimmermann, Riehen, Switzerland

[73] Assignee: Ciba-Geigy Corporation, Ardsley, N.Y.

[21] Appl. No.: 139,407

[22] Filed: Dec. 30, 1987

Related U.S. Application Data

[63] Continuation-in-part of Ser. No. 774,773, Sep. 11, 1985, abandoned.

[30] Foreign Application Priority Data

Sep. 14, 1984 [CH] Switzerland .................. 4388/84

[51] Int. Cl.⁴ .................. C07D 401/12; A61K 31/44
[52] U.S. Cl. .................. 514/318; 546/193; 546/194
[58] Field of Search .................. 514/318; 546/193, 194

[56] References Cited

U.S. PATENT DOCUMENTS 4,656,181 4/1987 Sunkel et al. .................. 514/336

FOREIGN PATENT DOCUMENTS 174654 3/1986 European Pat. Off. .

Primary Examiner—Jane T. Fan
Attorney, Agent, or Firm—JoAnn Villamizar; Irving M. Fishman

[57] ABSTRACT

Compounds of the formula

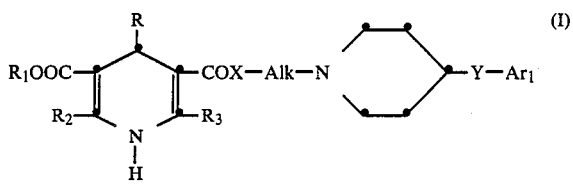

in which
R represents a carbocyclic or heterocyclic aryl radical,
$R_1$ represents lower alkyl, one of the groups $R_2$ and $R_3$ represents lower alkyl and the other represents lower alkyl, cyano or amino,
X represents oxygen or the group —NH—, and
Alk represents lower alkylene which separates the group X from the ring nitrogen atom by at least two carbon atoms,
Y represents the group —CHOH— or —(C=O)—, and
$Ar_1$ represents a monocyclic aryl or heteroaryl radical,
$Ar_1$ being other than unsubstituted phenyl if $R_1$, $R_2$ and $R_3$ each represents lower alkyl, X represents oxygen, Alk represents straight-chain alkylene having from 2 to 4 carbon atoms, Y represents the group —(C=O)— and R has the meaning given, and salts thereof have cardiovascular, especially coronary-dilatory and antihypertensive properties.

21 Claims, No Drawings

3,5-DIACYL-4-ARYL-1,4 DIHYDROPYRIDINE DERIVATIVES, THEIR USES AND COMPOSITIONS

This is a continuation-in-part of U.S. patent application Ser. No. 774,773, filed Sept. 11, 1985 now abandoned This invention relates to novel carbonyl compounds and salts thereof, processes for their manufacture, pharmaceutical preparations containing them and the use thereof.

The compounds according to the invention correspond to the formula

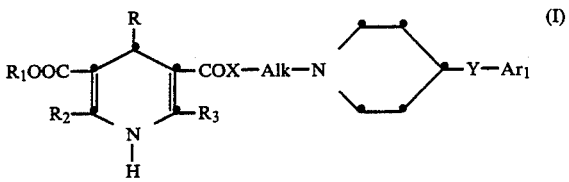

in which
- R represents a carbocyclic or heterocyclic aryl radical,
- $R_1$ represents lower alkyl, one of the groups $R_2$ and $R_3$ represents lower alkyl and the other represents lower alkyl, cyano or amino,
- X represents oxygen or the group —NH—, and
- Alk represents lower alkylene which separates the group X from the ring nitrogen atom by at least two carbon atoms,
- Y represents the group —CHOH— or —(C=O)—, and
- $Ar_1$ represents a monocyclic aryl or heteroaryl radical,
- $Ar_1$ being other than unsubstituted phenyl if
- $R_1$, $R_2$ and $R_3$ each represents lower alkyl, X represents oxygen, Alk represents straight-chain alkylene having from 2 to 4 carbon atoms, Y represents the group —(C=13)— and R has the meaning given; the invention also provides salts of compounds of the formula I.

A carbocyclic or heterocyclic aryl radical R is especially a corresponding monocyclic radical, but can also be a bi- or poly-cyclic, carbocyclic or heterocyclic radical having aromatic properties.

Carbocyclic radicals R of this kind are especially optionally substituted phenyl, and also naphthyl.

Heterocyclic aryl radicals R are preferably corresponding monocyclic radicals, but can also be corresponding bi- or poly-cyclic radicals, it being possible for the latter to consist of several heterocyclic rings, or of one or more rings having one or more fused carbocyclic rings, especially one or more fused benzo rings. The heterocyclic radicals R usually present, which preferably consist of five or six ring members, may contain as ring members up to four identical or different hetero atoms, especially nitrogen, oxen and/or sulphur atoms, preferably one, two, three or four nitrogen atoms, an oxygen or sulphur atom, or one or two nitrogen atoms together with an oxygen or sulphur atom. They are bonded, customarily via a ring carbon atom, to the carbon atom in the 4-position of the 1,4-dihydropyridine ring.

Monocyclic five-membered heteroaryl radicals R are, for example, corresponding monoaza-, diaza-, triaza-, tetraza-, monooxa-, monothia-, oxaza-, oxadiaza-, thiaza- or thiadiaza-cyclic radicals, such as pyrryl, pyrazolyl, imidazolyl, triazolyl, tetrazolyl, furyl, thienyl, isoxazolyl, oxazolyl, oxadiazolyl, isothiazolyl, thiazolyl or thiadiazolyl radicals, whilst monocyclic six-membered heteroaryl radicals R are, for example, corresponding monoaza-, diaza- or triaza-cyclic radicals, such as pyridyl, pyridazinyl, pyrimidinyl, pyrazinyl or triazinyl radicals. Bicyclic heteroaryl radicals are especially monocyclic heteroaryl radicals with a fused benzo ring; the hetero ring may be five- or six-membered, a five-membered heteroaryl radical being, for example, a monoaza-, diaza-, diaza-monooxa-, monooxa-, monothia-, oxaza- or thiaza-cyclic radical, and a six-membered heteroaryl radical being, for example, a monoaza- or a diaza-cyclic heteroaryl radical. Such bicyclic radicals, which may be bonded via a ring carbon atom of the hetero- or carbo-cyclic radical, are, for example, indolyl, isoindolyl, benzimidazolyl, benzoxadiazolyl, benzofuranyl, benzofurazanyl, benzothienyl, benzthiazolyl, benzthiadiazolyl, quinolinyl or isoquinolinyl radicals, it being possible for nitrogen-containing mono- or bi-cyclic heteroaryl radicals of the kind mentioned, especially unsubstituted or substituted pyridyl radicals, also to be present as N-oxides, for example pyridyl-N-oxide.

A monocyclic, carbocyclic aryl radical $Ar_1$ is especially an unsubstituted or a mono- or poly-substituted phenyl radical, whilst a monocyclic heteroaryl radical $Ar_1$ is, for example, a monocyclic monooxa-, monoaza-, or monothia-aryl radical, for example one as defined for R, especially furyl, pyrryl, pyridyl or thienyl each of which is unsubstituted or mono- or poly-substituted by the same or different substituents.

The carbocyclic and heterocyclic aryl radicals R and $Ar_1$ may be unsubstituted or substituted, it being possible especially for ring carbon atoms, but also for ring nitrogen atoms, to be substituted by from one to three of the same or different substituents, but they are preferably mono-substituted. Substituents of ring carbon atoms are, inter alia, optionally substituted hydrocarbon radicals, such as corresponding aliphatic, cycloaliphatic, aromatic or araliphatic hydrocarbon radicals, for example lower alkyl, lower alkenyl, lower alkynyl, lower alkylene, cycloalkyl, cycloalkyl-lower alkyl, phenyl or phenyl-lower alkyl. Substituents of such hydrocarbon radicals, especially of lower alkyl, phenyl or phenyl-lower alkyl, are, for example, optionally etherified or esterified hydroxy groups, such as hydroxy, lower alkoxy optionally substituted, for example, by optionally etherified or esterified hydroxy, for example lower alkoxy, lower alkoxy-lower alkoxy, or halo-lower alkoxy, lower alkenyloxy optionally substituted, for example, by optionally etherified or esterified hydroxy, for example lower alkenyloxy or halo-lower alkenyloxy, lower alkynyloxy, lower alkylenedioxy, lower alkanoyloxy or halogen, and/or optionally functionally modified carboxy, such as carboxy, esterified carboxy, for example lower alkoxycarbonyl, amidated carboxy, such as carbamoyl, N-lower alkyl-carbamoyl, N,N-di-lower alkylcarbamoyl, or cyano. Cyclic substituents, especially phenyl, may in addition also contain as substituent(s) lower alkyl that may optionally be substituted, for example as indicated. Further substituents of aryl radicals R and $Ar_1$ are, for example, optionally etherified or esterified hydroxy groups, such as hydroxy, lower alkoxy optionally substituted, for example, by optionally etherified or esterified hydroxy, for example lower alkoxy, lower alkoxy-lower alkoxy or halo-lower alkoxy, lower alkenyloxy optionally substituted, for example, by optionally etherified or esterified hydroxy, for example lower alkenyloxy or halo-lower alkenyloxy, lower alkynyloxy, lower alkylenedioxy, lower alkanoyloxy or halogen, nitro, optionally substituted amino, such as amino, N-lower alkylamino, N,N-di-lower alkylamino, N-lower alkyl-N-phenyl-lower alkylamino, lower alkyleneamino, oxa-lower alkyleneamino, thia-lower alkyleneamino or aza-lower alkyleneamino, it being possible for the aza nitrogen to be unsubstituted or substituted, for example, by lower alkyl, phenyl or phenyl-lower alkyl each of which is optionally substituted, for example, as described above, or acylamino, for example lower alkanoylamino, azido, acyl, such as lower alkanoyl, or optionally functionally modified carboxy, such as carboxy, esterified carboxy, for example lower alkoxycarbonyl, or amidated carboxy, such as carbamoyl, N-lower alkyl-carbamoyl or N,N-di-lower alkyl-carbamoyl, also cyano, optionally functionally modified sulpho, such as sulpho, aminosulphonyl, N-lower alkylaminosulphonyl or N,N-di-lower alkylaminosulphonyl and/or etherified mercapto, which may optionally be oxidised, such as lower alkylthio, lower alkylsulphinyl or lower alkylsulphonyl. Substituents of ring nitrogen atoms are especially the above-mentioned optionally substituted hydrocarbon radicals, such as lower alkyl, and also hydroxy or oxido.

Heterocyclic aryl radicals R and Ar₁ may, for example depending on the nature of the substitution, be present in various tautomeric forms.

The alkylene radical Alk separates the group X from the ring nitrogen atom preferably by from 2 to 8 carbon atoms and is, for example, ethylene, 1,2- or 1,3-propylene, 1,4-butylene, 1,5-pentylene or 1,6-hexylene.

The definitions used hereinbefore and hereinafter, unless expressly defined otherwise, have the following meanings:

The expression "lower" means that correspondingly defined groups or compounds, unless defined otherwise, contain up to and includiing 7, preferably up to and including 4, carbon atoms.

Substituted radicals may contain one or more identical or different substituents; these can occupy any suitable position.

Naphthyl may be 1- or 2-naphthyl.

Pyrryl is, for example, 2- or 3-pyrryl, pyrazolyl is, for example, 3- or 4-pyrazolyl, imidazolyl is, for example, 2- or 4-imidazolyl, triazolyl is, for example, 1,3,5-1H-triazol-2-yl or 1,3,4-triazol-2-yl, and tetrazolyl is, for example, 1,2,3,4-1H-tetrazol-5-yl, whilst furyl is 2- or 3-furyl and thienyl is 2- or 3-thienyl. Isoxazolyl is, for example, 3-isoxazolyl, oxazolyl is, for example, 2- or 4-oxazolyl, oxadiazolyl is, for example, 1,3,4-oxadiazol-2-yl, isothiazolyl is, for example, 3-isothiazolyl, thiazolyl is 2- or 4-thiazolyl and thiadiazolyl is, for example, 1,3,4-thiadiazol-2-yl.

Pyridyl is 2-, 3- or 4-pyridyl, pyridazinyl is, for example, 3-pyridazinyl, pyrimidinyl is 2-, 4- or 5-pyrimidinyl, pyrazinyl is 2-pyrazinyl and triazinyl is, for example, 1,3,5-triazin-2-yl.

Indolyl is, for example, 2-, 3- or 5-indolyl, isoindolyl is, for example 1-isoindolyl, benzimidazolyl is, for example, 2- or 5-benzimidazolyl, benzofuranyl is, for example, 2- or 3-benzofuranyl, benzofurazanyl (also 2,1,3-benzoxadiazolyl) is, for example, 4-benzofurazanyl, benzothienyl is, for example, 3-benzothienyl, benzthiazolyl is, for example, 2-benzthiazolyl, 2,1,3-benzthiadiazolyl is, for example 2,1,3-benzthiadiazol-4-yl, quinolinyl is, for example, 2- or 4-quinolinyl, and isoquinolinyl is, for example, 1-isoquinolinyl.

Lower alkyl is, for example, methyl, ethyl, n-propyl, isopropyl, n-butyl, isobutyl or tert.-butyl, also n-penty, n-hexyl or n-heptyl, whilst lower alkenyl is, for example, allyl or methallyl, and lower alkynyl is, for example, propargyl.

Cycloalkyl preferably has from 5 to 7 ring carbon atoms and is, for example, cyclopentyl or cyclohexyl, whilst cycloalkyl-lower alkyl may be, for example, cyclopropylmethyl, cyclopentylmethyl or cyclohexylmethyl.

Phenyl-lower alkyl is, for example, benzyl or 1-or 2-phenylethyl.

Lower alkoxy is especially methoxy, ethoxy, n-propoxy, isopropoxy, n-butoxy, isobutoxy or tert.-butoxy.

In a lower alkoxy-lower alkoxy radical, the terminal lower alkoxy group is preferably separated by more than one carbon atom from the linking oxygen atom; such radicals are, for example, 2-methoxyethoxy or 2-ethoxyethoxy.

One or more halogen atoms which preferably have an atomic number of up to 35, and are especially fluorine and/or chlorine, may be present in a halo-lower alkoxy radical; such a radicals are, for example, difluoromethoxy or 1,1,2-trifluoro-2-chloroethoxy.

Lower alkenyloxy is, for example, allyloxy or methallyloxy, and halo-lower alkenyloxy, which may contain one or more halogen atoms, the latter preferably having an atomic number of up to 35 and representing especially fluorine and/or chlorine, is, for example, 1,2-dichlorovinyloxy.

Lower alkynyloxy is, for example, propargyloxy, whilst lower alkylenedioxy is, for example, methylenedioxy or ethylenedioxy.

Lower alkylene is, for example, 1,2-ethylene or 1,3-propylene, whilst lower alkylenedioxy is, for example, methylenedioxy or 1,2-ethylenedioxy.

Lower alkanoyloxy is, for example, acetoxy, propionyloxy or pivaloyloxy.

Halogen preferbly has an atomic number of up to and including 35 and is especially fluorine or chlorine, or may be bromine, but can also be iodine.

Halo-substituted lower alkyl is, for example, trifluoromethyl, 1,1,2-trifluoro-2-chloroethyl or chloromethyl.

Lower alkoxycarbonyl is, for example, methoxycarbonyl, ethoxycarbonyl, n-propoxycarbonyl, isopropoxycarbonyl, n-butoxycarbonyl, isobutoxycarbonyl or tert.-butoxycarbonyl.

N-lower alkylcarbamoyl is, for example, N-methyl-carbamoyl or N-ethyl-carbamoyl, whilst N,N-di-lower alkyl-carbamoyl is, for example, N,N-dimethyl-carbamoyl or N,N-diethyl-carbamoyl.

N-lower alkylamino is, for example, N-methylamino, N-ethylamino, N-n-propylamino or N-isopropylamino.

N,N-di-lower alkylamino is, for example, N,N-dimethylamino, N-ethyl-N-methylamino or N,N-diethylamino, whilst N-lower alkyl-N-phenyl-lower alkylamino is, for example, N-benzyl-N-methylamino or N-methyl-N-(2-phenylethyl)-amino.

Lower alkyleneamino preferably contains from 4 to 6 ring carbon atoms and is, for example, pyrrolidino or piperidino, whilst oxa-lower alkyleneamino may be, for example, 4-morpholino, thia-lower alkyleneamino may be, for example, 4-thiomorpholino and optionally aza-substituted aza-lower alkyleneamino may be, for example, piperazino, 4-methylpiperazino, 4-phenylpiperazino, 4-benzylpiperazino or 4-(2-phenylethyl)-piperazino.

Lower alkanoylamino is, for example, acetylamino or propionylamino.

Lower alkanoyl is, for example, formyl, acetyl, propionyl or pivaloyl.

Lower alkylthio is, for example, methylthio, ethylthio, n-propylthio or isopropylthio, whilst lower alkylsulphinyl is, for example, methylsulphinyl and lower alkylsulphonyl is, for example, methylsulphonyl or ethylsulphonyl.

N-lower alkylaminosulphonyl is, for example, N-methylaminosulphonyl, whilst N,N-di-lower alkylaminosulphonyl is, for example, N,N-dimethylaminosulphonyl.

In a substituted lower alkoxycarbonyl radical the substituent is usually separated from the oxygen atom by at least 2, and preferably 2 or 3, carbon atoms. Such radicals are, for example, hydroxy-lower alkoxycarbonyl, such as 2-hydroxyethoxycarbonyl or 2,3-dihydroxypropoxycarbonyl, lower alkoxy-lower alkoxycarbonyl, for example 2-methoxyethoxycarbonyl, di-lower alkylamino-lower alkoxycarbonyl, for example 2-dimethylaminoethoxycarbonyl, 2-diethylaminoethoxycarbonyl or 3-dimethylaminopropoxycarbonyl, lower alkyleneamino-lower alkoxycarbonyl, for example 2-pyrrolidinoethoxycarbonyl or 2-piperidinoethoxycarbonyl, morpholino-lower alkoxycarbonyl, for example 2-(4-morpholino)-ethoxycarbonyl, or (4-lower alkyl-piperazino)-N-lower alkoxycarbonyl, for example 2-(4-methylpiperazino)-ethoxycarbonyl.

Phenyl-lower alkoxycarbonyl is, for example, benzyloxycarbonyl or 2-phenylethoxycarbonyl.

N,N-lower alkylene-carbamoyl is, for example, pyrrolidinocarbonyl or piperidinocarbonyl, corresponding radicals in which the lower alkylene moiety is interrupted by oxygen, sulphur or unsubstituted or substituted nitrogen being, for example, 4-morpholinocarbonyl, 4-thiomorpholinocarbonyl, 1-piperazinocarbonyl, or 4-methyl-1-piperazinocarbonyl.

Compounds of the formula I may be in the form of salts, especially acid addition salts, in particular corresponding pharmaceutically acceptable non-toxic acid addition salts. Such salts are, for example, those with hydrohalic acids, for example hydrochloric or hydrobromic acid, also nitric acid, sulphuric acid or phosphoric acid, or organic acids, such as carboxylic acids, for example acetic acid, propioninc acid, glycolic acid, succinic acid, maleic acid, hydroxymaleic acid, methylmaleic acid, fumaric acid, malic acid, tartaric acid, citric acid, benzoic acid, cinnamic acid, mandelic acid, salicyclic acid, 4-aminosalicylic acid, 2-phenoxybenzoic acid, 2-acetoxybenzoic acid, embonic acid, nicotinic acid or isonicotinic acid, also amino acids, or organic sulphonic acids, such as optionally hydroxy-containing lower alkanesulphonic acids, for example methanesulphonic acid, ethanesulphonic acid, 2-hydroxyethanesulphonic acid or ethane-1,2-disulphonic acid, or arylsulphonic acids, for example benzenesulphonic acid, 4-methylbenzenesulphonic acid or naphthalene-2-sulphonic acid, or with other acidic organic substances, such as ascorbic acid.

The compounds of the formula I and the salts thereof have valuable pharmacological properties, especially in the cardiovascular field. They are effective as calcium-antagonists and have α-receptor-blocking and serotonin-antagonistic properties, as may be demonstrated, for example, in in vitro tests on isolated-perfused mesenteric layer of rats [McGregor D. D.: J. Physiol. 177, 21-30 (1965)] in the form of inhibition of calcium-, noradrenalin- and serotonin-induced vasoconstriction, for example using 2,6-dimethyl-4-(3-nitrophenyl)-1,4-dihydropyridine-3,5-dicarboxylic acid methyl ester-2-[4-(p-fluorobenzoyl)-piperidino]-ethyl ester hydrochloride or 2,6-dimethyl-4-(3-nitrophenyl)-1,4-dihydropyridine-3-carboxylic acid methyl ester-5-N-[2-[4-(p-fluorobenzoyl)-piperidino]-ethyl]-carboxamide hydrochloride in a concentration range of from approximately $5 \times 10^{-10}$ mol/liter to approximately $10^{-8}$ mol/liter.

Furthermore, it is possible to detect the bonding of the novel compounds or the salts thereof to dihydropyridine receptors by the displacement of the bonding of $^3$H-nitrendipin to membranes of guinea pig hearts in in vitro tests [Erne P. et al.,: Biochem., Biophys. Res. Comm., 118, 842-847 (1984)], for example using 2,6-dimethyl-4-(3-nitrophenyl)-1,4-dihydropyridine-3,5-dicarboxylic acid methyl ester-2-[4-(p-fluorobenzoyl)-piperidino]-ethyl ester hydrochloride or 2,6-dimethyl-4-(3-nitrophenyl)-1,4-dihydropyridine-3-carboxylic acid methyl ester-5-N-[2-[4-(p-fluorobenzoyl)-piperidino]-ethyl]-carboxamide hydrochloride in a concentration range of from approximately $10^{-10}$ mol/liter to approximately $10^{-7}$ mol/liter. The novel compounds and the salts thereof also have an anti-hypertensive activity, as can be demonstrated, for example, by the reduction in blood pressure in renally hypertensive rats in a dosage range of approximately 1-100 mg/kg p.o.

Thus, for example, 2 hours after p.o. administration of 60 mg/kg of 2,6-dimethyl-4-(3-nitrophenyl)-1,4-dihydropyridine-3-carboxylic acid methyl ester-5-N-[2-[4-(p-fluorobenzoyl)-piperidino]-ethyl]-carboxamide hydrochloride to a renally hypertensive rat, a reduction in blood pressure of approximately 50 mm Hg can be observed.

The compounds of the formula I and salts of such compounds can therefore be used, for example, as coronary dilators and antihypertensives for the treatment of cardiovascular conditions, such as *Angina pectoris* and its sequelae, vascular constrictions, central and peripheral circulatory disorders, high blood pressure, arrhythmia and cardiac insufficiency, and also for the inhibition of platelet aggregation. The novel compounds are, however, also valuable intermediates for the manufacture of other compounds, especially pharmaceutically active compounds.

The invention relates especially to novel compounds of the formula I in which R represents a mono- or bicyclic, carbocyclic aryl radical, or a five- or six-membered monocyclic heteroaryl radical containing as ring members from one up to and including four ring nitrogen atoms, a ring oxygen or ring sulphur atom, or one or two ring nitrogen atoms together with a ring oxygen or a ring sulphur atom, which radical is bonded via a ring carbon atom to the carbon atom in the 4-position of the 1,4-dihydropyridine ring, optionally contains a fused benzo ring, and represents especially phenyl, naphthyl, pyrryl, pyrazolyl, imidazolyl, triazolyl, tetrazolyl, furyl, thienyl, isoxazolyl, oxazolyl, oxadiazolyl, isothiazolyl, thiazolyl, thiadiazolyl, pyridyl, pyridazinyl, pyrimidinyl, pyrazinyl, triazinyl, indolyl, isoindolyl, benzimidazolyl, benzoxadiazolyl, benzofuranyl, benzofurazanyl, benzothienyl, benzthiazolyl, 2,1,3-benzthiadiazolyl, quinolinyl or isoquinolinyl, it being possible for ring carbon atoms in these radicals to be optionally substituted by: lower alkyl, lower alkenyl, lower alkynyl, lower alkylene, cycloalkyl, phenyl and/or phenyl-lower alkyl, it being possible for lower alkyl, phenyl or phenyl-lower alkyl optionally to contain as substituent(s) hydroxy, lower alkoxy, lower alkoxy-lower alkoxy, halo-lower alkoxy, lower alkenyloxy, halo-lower alkenyloxy, lower alkynyloxy, lower alkylenedioxy, lower alkanoyloxy, halogen, carboxy, lower alkoxycarbonyl, carbamoyl, N-lower alkylcarbamoyl, N,N-di-lower alkyl-carbamoyl and/or cyano, and for cyclic radicals also to contain as substituent(s) lower alkyl which may in turn be substituted as indicated; and/or by hydroxy, lower alkoxy, lower alkoxy-lower alkoxy, halo-lower alkoxy, lower alkenyloxy, halo-lower alkenyloxy, lower alkynyloxy, lower alkylenedioxy, lower alkanoyloxy, halogen, nitro, amino, N-lower alkylamino, N,N-di-lower alkylamino, N-lower alkyl-N-phenyl-lower alkylamino, lower alkyleneamino, oxa-lower alkyleneamino, thia-lower alkyleneamino and/or aza-lower alkyleneamino in which the aza nitrogen atom may be substituted by lower alkyl, phenyl or by phenyl-lower alkyl, it being possible for these radicals to contain as substituent(s) hydroxy, lower alkoxy, lower alkoxy-lower alkoxy, halo-lower alkoxy, lower alkenyloxy, halo-lower alkenyloxy, lower alkynyloxy, lower alkylenedioxy, lower alkanoyloxy, halogen, carboxy, lower alkoxycarbonyl, carbamoyl, N-lower alkylcarbamoyl, N,N-di-lower alkyl-carbamoyl and/or cyano, and for the cyclic radicals also to contain lower alkyl as substituent(s); and/or by lower alkanoylamino, azido, lower alkanoyl, carboxy, lower alkoxycarbonyl, carbamoyl, N-lower alkyl-carbamoyl, N,N-di-lower alkylcarbamoyl, cyano, sulpho, aminosulphonyl, N-lower alkylaminosulphonyl, N,N-di-lower alkylaminosulphonyl, lower alkylthio, lower alkylsulphinyl and/or lower alkylsulphonyl; and/or for ring nitrogen atoms to be optionally substituted by lower alkyl that may optionally contain as substituent(s) hydroxy, lower alkoxy, lower alkoxy-lower alkoxy, halo-lower alkoxy, lower alkenyloxy, halo-lower alkenyloxy, lower alkynyloxy, lower alkylenedioxy, lower alkanoyloxy, halogen, carboxy, lower alkoxycarbonyl, carbamoyl, N-lower alkyl-carbamoyl, N,N-di-lower alkyl-carbamoyl and/or cyano, or by hydroxy or oxido, $R_1$ represents lower alkyl, one of the radicals $R_2$ and $R_3$ represents lower alkyl and the other represents lower alkyl, cyano or amino, X represents oxygen or the group —NH— and Alk represents lower alkylene which separates the group X from the ring nitrogen atom by from 2 to 8 carbon atoms, Y represents a group of the formula —CHOH— or, especially, —(C=O)— and $Ar_1$ represents a monocyclic carbocyclic aryl or heteroaryl radical and is especially phenyl, naphthyl, pyrryl, furyl, thienyl, or pyridyl, ring carbon atoms in these radicals being optionally substituted by: lower alkyl, lower alkenyl, lower alkynyl, lower alkylene, cycloalkyl, phenyl and/or phenyl-lower alkyl, it being possible for lower alkyl, phenyl or phenyl-lower alkyl to contain as substituent(s) hydroxy, lower alkoxy, lower alkoxy-lower alkoxy, halo-lower alkoxy, lower alkenyloxy, halo-lower alkenyloxy, lower alkynyloxy, lower alkylenedioxy, lower alkanoyloxy, halogen, carboxy, lower alkoxycarbonyl, carbamoyl, N-lower alkylcarbamoyl, N,N-di-lower alkyl-carbamoyl and/or cyano, and for cyclic radicals also to contain lower alkyl which may in turn be substituted as indicated; and/or by hydroxy, lower alkoxy, lower alkoxy-lower alkoxy, halo-lower alkoxy, lower alkenyloxy, halo-lower alkenyloxy, lower alkynyloxy, lower alkylenedioxy, lower alkanoyloxy, halogen, nitro, amino, N-lower alkylamino, N,N-di-lower alkylamino, N-lower alkyl-N-phenyl-lower alkylamino, lower alkyleneamino, oxo-lower alkyleneamino, thia-lower alkyleneamino and/or aza-lower alkyleneamino in which the aza nitrogen atom may be substituted by lower alkyl, phenyl or by phenyl-lower alkyl, it being possible for these radicals to contain as substituent(s) hydroxy, lower alkoxy, lower alkoxy-lower alkoxy, halo-lower alkoxy, lower alkenyloxy, halo-lower alkenyloxy, lower alkynyloxy, lower alkylenedioxy, lower alkanoyloxy, halogen, carboxy, lower alkoxycarbonyl, carbamoyl, N-lower alkylcarbamoyl, N,N-di-lower alkyl-carbamoyl and/or cyano, and for the cyclic radicals also to contain lower alkyl as substituent(s); and/or by lower alkanoylamino, azido, lower alkanoyl, carboxy, lower alkoxycarbonyl, carbamoyl, N-lower alkyl-carbamoyl, N,N-di-lower alkylcarbamoyl, cyano, sulpho, aminosulphonyl, N-lower alkylaminosulphonyl, N,N-di-lower alkylaminosulphonyl, lower alkylthio, lower alkylsulphinyl and/or lower alkylsulphonyl; and/or for ring nitrogen atoms to be optionally substituted by lower alkyl which may optionally contain as substituent(s) hydroxy, lower alkoxy, lower alkoxy-lower alkoxy, halo-lower alkoxy, lower alkenyloxy, halo-lower alkenyloxy, lower alkynyloxy, lower alkylenedioxy, lower alkanoyloxy, halogen, carboxy, lower alkoxycarbonyl, carbamoyl, N-lower alkyl-carbamoyl, N,N-di-lower alkylcarbamoyl and/or cyano, or by hydroxy or oxido; $Ar_1$ being other than unsubstituted phenyl if $R_1$, $R_2$ and $R_3$ each represents lower alkyl, X represents oxygen, Alk represents straight-chain alkylene having from 2 to 4 carbon atoms, Y is the group —(C=O)— and R has the meaning given, and to salts, especially pharmaceutically acceptable non-toxic acid addition salts, of such compounds.

The invention relates especially to novel compounds of the formula I in which R and $Ar_1$ each represents phenyl or naphthyl which is optionally substituted by lower alkyl, phenyl and/or phenyl-lower alkyl, it being possible for such radicals themselves to contain as substituent(s) hydroxy, lower alkoxy, halo-lower alkoxy, lower alkylenedioxy, halogen, carboxy, lower alkoxycarbonyl and/or cyano, and for the cyclic radicals also to contain lower alkyl as substituent(s); and/or by hydroxy, lower alkoxy, halo-lower alkoxy, lower alkenyloxy, halo-lower alkenyloxy, lower alkylenedioxy, halogen, nitro, amino, N-lower alkylamino, N,N-di-lower alkylamino, lower alkanoylamino, carboxy, lower alkoxycarbonyl, carbamoyl, cyano, sulpho, aminosulphonyl, N-lower alkylaminosulphonyl, N,N-di-lower alkylaminosulphonyl, lower alkylthio, lower alkylsulphinyl and/or lower alkylsulphonyl, R may in addition represent pyrryl, furyl, thienyl, pyridyl, 1-oxidopyridyl, imidazolyl, benzofurazanyl or benzoxadiazolyl each bonded via a ring carbon atom, and $Ar_1$ may in addition represent pyrryl, furyl, thienyl or pyridyl each bonded via a ring carbon atom; such radicals R and/or $Ar_1$ are optionally substituted as indicated for a phenyl or naphthyl radical R and $Ar_1$, respectively, and may contain as substituent(s) especially lower alkyl, lower alkoxy, halogen and/or phenyl optionally substituted by lower alkyl, lower alkoxy, halogen and/or nitro; $R_1$ represents lower alkyl, $R_2$ and $R_3$ each represents lower alkyl, or one of the groups $R_2$ and $R_3$ represents lower alkyl and the other represents lower alkyl or cyano, X represents oxygen or the group —NH— and Alk represents the group —$(CH_2)_n$— in which n is an integer of from 2 to 6, and Y represents a group of the formula —CHOH— or, especially, —(C=O)—, $Ar_1$ being other than unsubstituted phenyl if $R_1$, $R_2$ and $R_3$ each represents lower alkyl, X represents oxygen, n represents an integer of from 2 to 4, Y represents the group —(C=O)— and R has the meaning given, and to salts, especially pharmaceutically acceptable non-toxic acid addition salts, of such compounds.

The invention relates most especially to novel compounds of the formula I in which R and $Ar_1$ each represents phenyl, which is optionally substituted by lower alkyl, for example methyl, hydroxy, lower alkoxy, for example methoxy or ethoxy, halo-lower alkoxy, for example difluoromethoxy or 2-chloro-1,1,2-trifluoroethoxy, halo-lower alkenyloxy, for example 1,2-dichlorovinyloxy, lower alkylenedioxy, for example methylenedioxy, halogen, for example fluorine, chlorine or bromine, trifluoromethyl, nitro, lower alkanoylamino, for example acetylamino, phenyl or phenyl-lower alkyl each optionally substituted by optionally esterified or etherified hydroxy, such as halogen, for example fluorine or chlorine, or lower alkoxy, for example methoxy, and/or by cyano, it being possible for a phenyl radical R or $Ar_1$ to contain one or more identical or different substituents, R may in addition represent pyridyl, for example 2-, 3- or 4-pyridyl, furyl, for example 2-furyl, 1-oxidopyridyl, for example 1-oxido-3-pyridyl, thienyl, for example 2-thienyl, or benzofurazanyl, for example 4-benzofurazanyl, and $Ar_1$ may in addition represent pyridyl, for example 2-, 3- or 4-pyridyl, furyl, for example 2-furyl, or thienyl, for example 2-thienyl, it being possible for such radicals R and $Ar_1$ to be substituted by lower alkyl, for example methyl, or halogen, for example fluorine or chlorine, $R_1$, $R_2$ and $R_3$ each represents lower alkyl, X represents especially oxygen, or also the group —NH—, Alk represents a group —$(CH_2)_n$— in which n represents an integer of from 2 to 4, and Y represents a group of the formula —CHOH— or, especially, —(C=O)—, $Ar_1$ being other than unsubstituted phenyl if $R_1$, $R_2$ and $R_3$ each represents lower alkyl, X represents oxygen, n is an integer of from 2 to 4, Y represents the group —(C=O)— and R has the meaning given, and to salts, especially pharmaceutically acceptable non-toxic acid addition salts, of such compounds.

The invention relates especially to novel compounds of the formula I in which R represents unsubstituted phenyl or preferably phenyl mono- or di-substituted by lower alkyl, for example methyl, lower alkoxy, for example methoxy, halo-lower alkoxy or halo-lower alkenyloxy in which halogen has an atomic number of up to and including 35 and is especially fluorine or chlorine, for example difluoromethoxy, halogen having an atomic number of up to and including 35, trifluoromethyl, nitro and/or by cyano, substituents usually occupying the 2- and/or the 3-position, $R_1$, $R_2$ and $R_3$ each represents lower alkyl, X represents especially oxygen, or also the group —NH—, Alk represents the group —$(CH_2)_n$— in which n is an integer of from 2 to 4, Y represents a group of the formula —CHOH— or, especially, —(C=O)—, and $Ar_1$ represents phenyl optionally substituted by halogen having an atomic number of up to and including 35, or pyridyl, for example 2-pyridyl, 3-pyridyl or 4-pyridyl, $Ar_1$ being other than unsubstituted phenyl if $R_1$, $R_2$ and $R_3$ each represents lower alkyl, X represents oxygen, n is an integer of from 2 to 4, Y represents the group —(C=O)— and R has the meaning given, and to salts, especially pharmaceutically acceptable non-toxic acid addition salts, of such compounds.

The invention relates especially to novel compounds of the formula I in which R represents phenyl mono- or di-substituted by halogen having an atomic number of up to and including 35, for example fluorine, chlorine or bromine, or phenyl mono-substituted by trifluoromethyl, nitro or cyano, substituents occupying the 2- and/or the 3-position, $R_1$ represents lower alkyl, especially methyl or ethyl, and $R_2$ and $R_3$ each represents lower alkyl, especially methyl, X represents oxygen, Alk represents the group —$(CH_2)_n$— in which n is 2 or 3, Y represents a group of the formula —(C=O)— and $Ar_1$ is phenyl optionally substituted by halogen having an atomic number of up to and including 35, for example fluorine, $Ar_1$ being other than unsubstituted phenyl if $R_1$, $R_2$ and $R_3$ each represents lower alkyl, X represents oxygen and n and R have the meanings given, and to salts, especially pharmaceutically acceptable non-toxic acid addition salts, of such compounds.

The invention relates especially to novel compounds of the formula I in which R represents phenyl mono- or di-substituted by halogen having an atomic number of up to and including 35, for example fluorine, chlorine or bromine, or preferably phenyl mono-substituted by nitro, or also by cyano, substituents occupying the 2- and/or the 3-position, $R_1$ represents lower alkyl, especially methyl or ethyl, and $R_2$ and $R_3$ each represents lower alkyl, especially methyl, X represents oxygen, Alk represents the group —$(CH_2)_n$— in which n is 2 or 3, Y represents the group —(C=O)— and $Ar_1$ represents phenyl substituted by halogen having an atomic number of up to and including 35, especially by fluorine, especially in the 4-position, and to salts, especially pharmaceutically acceptable non-toxic acid addition salts, of such compounds.

The invention relates especially to the specific compounds described in the Examples.

The compounds of the formula I and salts of such compounds having salt-forming properties may be manufactured in a manner known per se, for example as follows:

(a) a compound of the formula

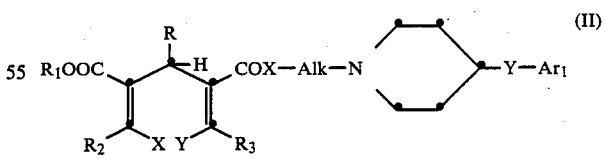

in which one of the radicals X and Y represents a group of the formula —$NH_2$ and the other represents hydroxy or a group of the formula —$NH_2$, or a tautomer thereof, or a corresponding tautomeric mixture, is ring-closed, or (b) a compound of the formula R—CHO (III) or a reactive functional derivative thereof is reacted with a compound of the formula

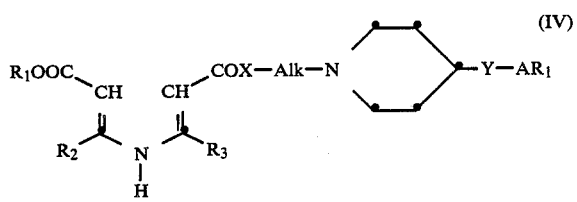

or a tautomer thereof or a corresponding tautomeric mixture, or (c) in a compound of the formula

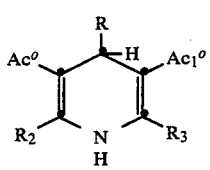

in which one of the radicals $Ac^o$ and $Ac_1^o$ represents a group that can be converted into the group —$COOR_1$ or into a radical of the formula

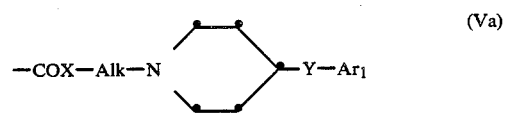

and the other represents the group —$COOR_1$ or a group of the formula Va, the radical $Ac^o$ or $Ac_1^o$ is converted into the group —$COOR_1$ or into a radical of the formula Va, as the case may be, or (d) a compound of the formula

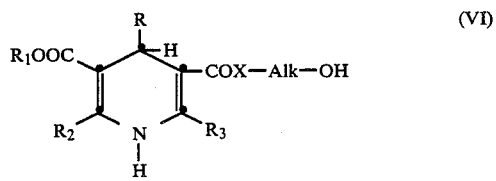

or a reactive ester thereof is reacted with a compound of the formula

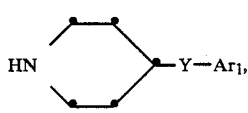

or (e) in a compound of the formula

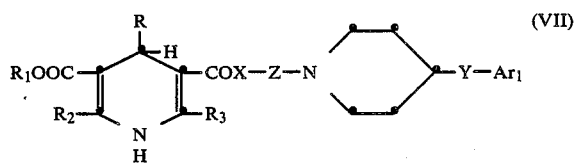

in which Z represents a group that can be converted into the group Alk by means of reduction, the group Z is reduced to the group Alk, it being possible for the starting materials of the formulae II to VII, insofar as they are capable of forming reactive derivatives or have salt-forming properties, also to be used in the form of reactive derivatives or in the form of their salts, and the symbols R, $R_1$, $R_2$, $R_3$, X, Y, $Ar_1$ and Alk have the meanings given under formula I and, if desired, a resulting compound of the formula I is converted into a different compound of the formula I and/or, if desired, a resulting salt is converted into the free compound or into a different salt and/or, if desired, a resulting free compound of the formula I is converted into a salt and/or, if desired, a resulting isomeric mixture is separated into the individual isomers.

Customarily, the starting materials of the formula II used in process variant (a) are formed in situ and the ring closure according to the process can take place under the reaction conditions for the manufacture of the starting material. For example, the starting materials of the formula II and, under the reaction conditions, customarily also the corresponding end products of the formula I, can be obtained by (aa) reacting a compound of the formula III, or a reactive functional derivative thereof, with a compound of the formula

and with a compound of the formula

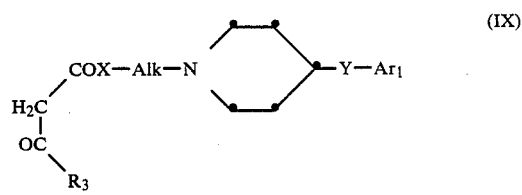

and ammonia, or (ab) reacting a compound of the formula III, or a reactive functional derivative thereof, with a compound of the formula

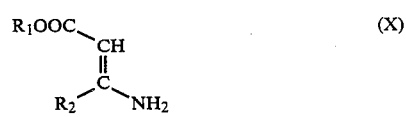

and with a compound of the formula IX, or (ac) reacting a compound of the formula III, or a reactive functional derivative thereof, with a compound of the formula

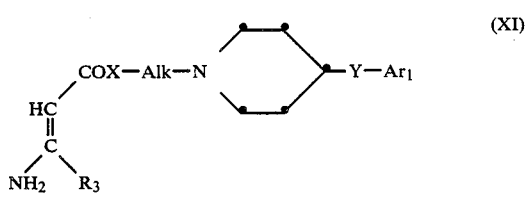

and with a compound of the formula VIII or X, or (ad) reacting ammonia with a compound of the formula

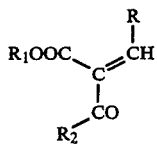

(XII)

and with a compound of the formula IX, or (ae) reacting ammonia with a compound of the formula

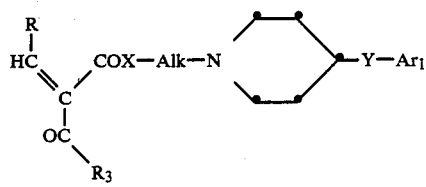

(XIII)

and with a compound of the formula VIII or X, or (af) reacting ammonia with a compound of the formula

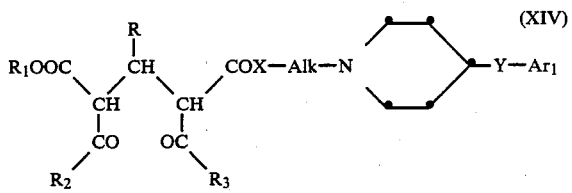

(XIV)

of (ag) reacting a compound of the formula X with a compound of the formula XIII or of the formula

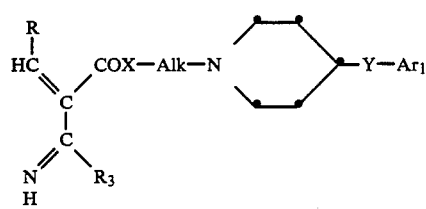

(XV)

or (ah) reacting a compound of the formula XI with a compound of the formula XII or with a compound of the formula

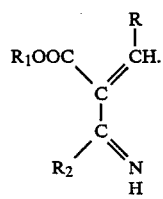

(XVI)

With the exception of the compound of the formula III, the compounds of the formula VIII to XVI may be used in the form of tautomers thereof or in the form of tautomeric mixtures; starting materials of the above formulae having salt-forming properties may also be used in the form of salts. Also, in the above compounds the groups, R, $R_1$, $R_2$, $R_3$, X, Y, $Ar_1$ and Alk have the meanings given in connection with formula I.

Reactive functional derivatives of the aldehyde of the formula III are, inter alia, the corresponding acetals, that is to say the di-(etherified hydroxy)methyl compounds corresponding to the group R, such as di-lower alkyl acetals, for example dimethyl or diethyl acetals, acylals, for example the corresponding di-acyloxymethyl or dihalomethyl compounds, such as di-lower alkanoyl acylals, for example diacetyl acylals, or the corresponding dihalo, for example dichloro or dibromo compounds, also addition compounds, such as those with an alkali metal bisulphite, for example potassium bisulphite.

The ammonia used for the ring closure reactions described hereinbefore may also be used in the form of an agent that yields this compound in situ, for example in the form of an ammonium salt, such as ammonium acetate or ammonium bicarbonate.

The ring closure reaction (a), and the condensation reactions (aa) to (ah) for the manufacture of the starting material for the ring closure reaction, customarily formed in situ, are variants of the dihydropyridine synthesis according to Hantzsch. In variant (aa), a total of three molecules of water are removed; in other variants instead of the removal of the elements of water there is in some cases an addition reaction, that is to say the removal of the elements of water has already occurred during the manufacture of one or two starting materials. In the reaction of compounds of the formula III with compounds of the formulae XI and X according to stage (ac), of compounds of the formula X with compounds of the formula XV according to stage (ag), or of compounds of the formula XI with compounds of the formula XVI according to stage (ah), ammonia is removed in addition to or instead of the elements of water. If, in accordance with variant (aa), compounds of the formula I are to be manufactured in which $R_2$ and $R_3$ are different from one another, by-products may result that contain the same substituents in the 2- and the 6-positions. By not using all the reactants together at the same time, the formation of such by-products can, however, be reduced by promoting a certain course of reaction which proceeds in situ according to another variant, since by adding the reactants in stages, for example, first of all a compound of the general formula X or of the formula XI may result.

The ring closure and condensation reactions according to the process are carried out in a manner known per se, if necessary in the presence of a condensation agent, especially a basic condensation agent, such as an excess of a basic reactant or of an additional, for example an organic, base, such as piperidine or ethyldiisopropylamine, or a metal alcoholate, such as an alkali metal lower alkoxide, and/or a suitable dehydrating or water-absorbing agent, also customarily in the presence of an inert organic solvent and at reaction temperatures in the range of from approximately room temperature to approximately 150° C., especially at the boiling temperature of the solvent. Optionally the reaction is carried out in an inert gas atmosphere, for example a nitrogen atmosphere, and/or, for example when using a low-boiling solvent and/or ammonia, in a closed vessel under elevated pressure.

The starting materials used in the process variants are known or can be manufactured according to processes known per se.

For example, starting materials of the formula IX can be manufactured in customary manner by reacting compounds of the formula

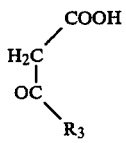 (IXa)

with compounds of the formula

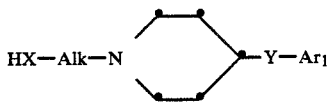 (IXb)

Instead of carboxylic acids of the formula IXa it is also possible to use functional derivatives thereof, such as corresponding carboxylic acid anhydrides, especially mixed anhydrides, such as those with lower alkanecarboxylic acids, for instance formic acid, also acid halides, for example corresponding chlorides, bromides, also acid azides, and, further, activated esters, for example cyanomethyl ester. These may be used, optionally in the presence of condensation agents, to form compounds of the formula IX by reaction with compounds of the formula IXb, and free carboxylic acids of the formula IXa may also be used to form compounds of the formula IX by reaction with compounds of the formula IXb in which the azido group replaces the group HX—. Carboxylic acids of the formula IXa may also be reacted in the form of salts, especially alkali metal salts or alkaline earth metal salts, with reactive esters of alcohols of the formula IXb in which X represents oxygen, such as corresponding halides, for example chlorides, bromides or iodides, or organic sulphonic acid esters, for example lower alkanesulphonic acid esters or arenesulphonic acid esters, such as methanesulphonic acid or p-toluenesulphonic acid esters, to form the corresponding carboxylic acid esters, or corresponding hydrolysable imino esters, such as corresponding imino-lower alkyl esters, are hydrolyzed to form the esters. Imino esters of this kind can be obtained in customary manner, for example from nitriles of the formula

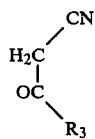 (IXc)

corresponding to the compounds of the formula IXa, by reaction with compounds of the formula IXb, in which X represents oxygen, in the presence of an acidic condensation agent, for instance hydrogen chloride, in a suitable solvent, for instance one of inert character, such as an aromatic substance, for example benzene.

Compounds of the formula IXb can in turn be obtained in a manner known per se, for example by reacting compounds of the formula

 HX—Alk—A (IXd), in which A represents a suitable leaving group, for example a reactive esterified hydroxy group, such as, for instance, halogen, for example chlorine, bromine or iodine, or a sulphonyloxy group, for example an arylsulphonyloxy group, such as a p-toluenesulphonyloxy group, with compounds of the formula

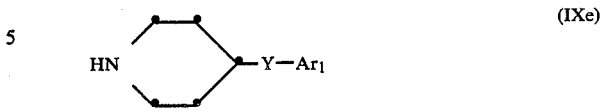 (IXe)

advantageously in the presence of a basic condensation agent, such as an oxide, hydroxide or carbonate of an alkali metal or alkaline earth metal, such as sodium hydroxide or calcium carbonate, customarily in the presence of a solvent, for instance a lower alkanol, such as ethanol, and at elevated or reduced temperature. Compounds of the formula IXe can also be used in the form of their metal derivatives in which the hydrogen atom positioned at the nitrogen is replaced y a suitable metal, for instance lithium or potassium. In such cases, the described reaction with compounds of the formula IXd is carried out in an inert anhydrous solvent, for instance one of ethereal character, such as tetrahydrofuran, or an aromatic solvent, for instance toluene.

Metal compounds corresponding to the formula IXe can be obtained in customary maner, for example by reaction with a suitable alkali metal organic compound, for instance butyllithium, in an anhydrous solvent, such as tetrahydrofuran, advantageously under a protective gas, for example argon, it being possible for the metal compound contained in the reaction mixture to be used for the above-described reaction without being isolated.

Compounds of the formula IXe can, in turn, be manufactured in a manner known per se, for instance from starting material that contain instead of the piperidine ring a suitable group that can be converted into a piperidine ring. Such groups are, for instance, those that form the piperidine ring, for example by means of reduction or by means of ring-closing condensation, for instance a corresponding 2-piperidone that can be converted by means of a suitable reducing agent, such as lithium aluminium hydride, into a starting material of the formula IXe. Or, for example, a corresponding 1,5-dihalopentane, for instance 1,5-dibromopentane, is used which, by means of ammonia, optionally in a closed vessel and under pressure, yields a starting material of the formula IXe.

The reaction of free carboxylic acids of the formula IXa with compounds of the formula IXb is advantageously carried out in the presence of an acidic catalyst that promotes removal of the elements of water, such as protonic acid, for example hydrochloric, hydrobromic, sulphuric, phosphoric or boric acid, benzenesulphonic ortoluenesulphonic acid, or a Lewis acid, for example boron trifluoride etherate, in an excess of the alcohol used and/or in an inert solvent, if necessary while removing the water freed during the reaction by distillation, for example azeotropic distillation. Furthermore, the reactions can also be carried out in the presence of water-binding condensation agents, such as suitably substituted carbodiimides, for example N,N'-diethyl-, N,N'-dicyclohexyl- or N-ethyl-N'-(3-dimethylaminopropyl)-carbodiimide, in inert organic solvents. Mixed anhydrides, especially acid halides, are reacted with alcohols or with alcoholates, for example alkali metal lower alkoxides, for example in the presence of acid-binding agents, for example organic, especially tertiary nitrogen, bases, such as triethylamine, ethyldiisopropylamine or pyridine, or also inorganic bases, for example alkali metal or alkaline earth metal hydroxides or carbonates, such as sodium, potassium or calcium hydroxide or carbonate.

The reactions of reactive esters, for example cyanomethyl or pentachlorophenyl esters, with compounds of the formula IXb are carried out, for example, in a solvent inert towards the reactants in a temperature range of from approximately 0° C. to approximately 120° C., preferably at from room temperature to approximately 60° C.

The hydrolysis of imido ester starting materials is carried out, for example, by means of water-containing mineral acids, such as hydrochloric acid or sulphuric acid, it being possible for the imino ester salts, for example hydrochlorides, obtained during the addition of hydrogen chloride to nitriles and the reaction with anhydrous alcohols, especially unsubstituted or substituted lower alkanols, to be hydrolysed directly to the corresponding esters after the addition of water. It is also possible, for example, to obtain the desired ester compound of the formula IX from a mixture of nitrile, alcohol and sulphuric acid with a suitable water content without isolation of the imido ester formed in situ.

Starting materials of the formulae XI, XIII, XIV and XV can be manufactured in analogous and customary manner from corresponding starting materials.

Starting materials of the formula IV are formed in situ in a manner analogous to that described for the manufacture of starting materials of the formula II, and the ring closure according to the process to form the end products of the formula I can be carried out under the conditions given for the manufacture of the starting materials in the same reaction mixture. Accordingly, starting materials of the formula IV can be obtained by reacting compounds of the formula IX with those of the formula VIII and ammonia, or by reacting compounds of the formula IX with those of the formula X, or by reacting compounds of the formula XI with those of the formula VIII or X, such reactions customarily being carried out in a suitable solvent, for instance a lower alkanol, such as ethanol, optionally at elevated or reduced temperature, and advantageously under a protective gas, such as nitrogen.

According to the radical(s) $Ac^o$ and/or $Ac_1^o$ contained in them, starting materials of the formula V may be, for example, carboxylic acids ($Ac^o$ and/or $Ac_1^o$ is (are) carboxy), carboxylic acid anhydrides, especially mixed anhydrides, such as acid halides, for example acid chlorides or bromides, or azides ($Ac^o$ and/or $Ac_1^o$ is (are) halocarbonyl, for example chloro- or bromo-carbonyl or azidocarbonyl), also activated esters, for example cyanomethyl esters ($Ac^o$ and/or $Ac_1^o$ is (are) cyanomethoxycarbonyl). These can be converted into the corresponding esters by treatment with a corresponding alcohol, optionally in the presence of condensation agents; for example, for the conversion of the group $Ac^o$ into a carboxy ester group corresponding to the group —$COOR_1$, reaction is carried out with a substituted or unsubstituted lower alkanol corresponding to the meaning of $R_1$, or with a reactive derivative thereof, for example a corresponding alcoholate, and in the case of free carboxylic acids reaction is carried out with suitable diazo compounds, such as unsubstituted or substitued diazolower alkanes, there being obtained compounds of the formula I that contain the group —$COOR_1$.

For the conversion of the group $Ac_1^o$ into the group of the above-defined formula Va, a starting material of the formula V is reacted with a compound of the formula IXb in customary manner. Carboxylic acid esters of the kind specified in which X represents oxygen can likewise be obtained if there are used as starting materials salts, especially alkali metal or alkaline earth metal salts, of the free carboxylic acids and these are treated with reactive esters of alcohols corresponding to the compounds of the formula IXb in which X represents oxygen, such as corresponding halides, for example chlorides, bromides or iodides, or organic sulphonic acid esters, for example lower alkanesulphonic acid esters or arenesulphonic acid esters, such as methanesulphonic acid esters or p-toluenesulphonic acid esters, or if corresponding hydrolysable imino esters, such as corresponding imino-lower alkyl esters, are hydrolysed to the esters.

Imino esters of this kind can be obtained, for example, from starting materials of the formula V in which $Ac^o$ and/or $Ac_1^o$ represent(s) the cyano group, by reaction with a lower alkanol corresponding to the meaning of $R_1$ and/or with an alcohol of the formula IXb in which X represents oxygen, in the presence of an acidic condensation agent, such as hydrogen chloride or concentrated sulphuric acid.

The reaction of free carboxylic acids with alcohols, such as unsubstituted or substituted lower alkanols, or with compounds of the formula IXb, is carried out advantageously in the presence of an acidic catalyst that promotes the removal of the elements of water, such as a protonic acid, for example hydrochloric, hydrobromic, sulphuric, phosphoric or boric acid, benzenesulphonic or toluenesulphonic acid, or a Lewis acid, for example boron trifluoride etherate, in an excess of the alcohol used or of the compound of the formula IXb and/or in an inert solvent, if necessary while removing the water freed during the reaction by distillation, for example azeotropic distillation. Furthermore, it is also possible to carry out the reactions in the presence of water-binding condensation agents, such as suitably substituted carbodiimides, for example N,N'-diethyl-, N,N'-dicylohexyl- or N-ethyl-N'-(3-dimethylaminopropyl)-carbodiimide, customarily in inert organic solvents. Mixed anhydrides, especially acid halides, are reacted, for example, in the presence of acid-binding agents, for example organic, especially tertiary, nitrogen bases, such as triethylamine, ethyldiisopropylamine or pyridine, or also inorganic bases, for example alkali metal or alkaline earth metal hydroxides or carbonates, such as sodium, potassium or calcium hydroxide or carbonate, with alcohols or with alcoholates, for example alkali metal lower alkoxides.

The reactions of reactive esters corresponding to the formula V, for example cyanomethyl, benztriazol-1-yl or pentachlorophenyl esters, with lower alkanols corresponding to the meaning of $R_1$ or with compounds of the formula IXb are carried out, for example, in a solvent inert towrds the reactants in a temperature range of from approximately 0° C. to approximately 120° C., preferably at from room temperature to approximately 60° C.

The hydrolysis of imido ester starting materials is carried out, for example, by means of water-containing mineral acids, such as hydrochloric acid or sulphuric acid, it being possible, for example, for the imino ester salts, for example imino ester hydrochlorides, obtained by the addition of hydrogen chloride to nitriles and reaction with anhydrous alcohols, especially unsubstituted or substituted lower alkanols, to be hydrolysed directly to the corresponding esters after the addition of water. It is also possible, for example, to obtain the desired ester compound of the formula I from a mixture of nitrile, alcohol and sulphuric acid with a suitable water content without isolation of the imido ester formed in situ.

Starting materials of the formula V having a free carboxy group $Ac^o$ and/or $Ac_1^o$ can be obtained, for example, by manufacturing the corresponding 2-cyanoethyl ester, there being used, for example in one of the above-described processes (ab) to (ag), a compound of the formula X in which there is a 2-cyanoethoxycarbonyl group in place of the —$COOR_1$ group; for example, a 3-aminocrotonic acid 2-cyanoethyl ester containing the group $R_2$ may be reacted with the other reactants and then the resulting 2-cyanoethyl ester compound may be cleaved to form the free carboxylic acid under mild conditions, for example by means of aqueous or aqueous-lower alkanolic 1N sodium hydroxide at room temperature. The free carboxylic acid can, if necessary, be converted in a manner known per se into the desired reactive functional derivatives.

The nitrile compounds of the formula V that also come into consideration as starting materials for process variant (c) can be manufactured, for example, analogously to one of the process variants (aa) to (ah) by using starting materials that contain a cyano group instead of the radical —$COOR_1$ or the group of the formula IXb, such as, for example, by using instead of a compound of the formula X a 3-aminocrotonitrile containing the group $R_2$.

The starting materials of the formula VI required for process variant (d) can be manufactured in a manner known per se, for example analogously to the reactions described in the process stages (aa) to (ah), there being used instead of compounds IX, XI, XIII, XIV or XV starting materials that contain instead of the group of the formula

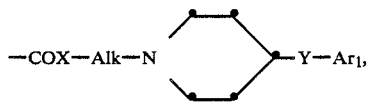
(VIa)

a group of the formula —COX—Alk—OH (VIb) or a reactive ester thereof. Reactive esters are, for example, those esters formed with a hydrohalic acid, for example hydrochloric acid, or an organic sulphonic acid, such as an arylsulphonic acid, for example p-toluenesulphonic acid, in which the hydroxy group is replaced, for example, by halogen, such as chlorine or bromine, or, for example, by arylsulphonyloxy, such as p-toluenesulphonyloxy. For example, a starting material of the formula

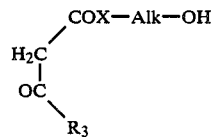
(VIc)

can be obtained analogously to the methods described for the manufacture of starting materials of the formula IX, for example by reacting a compound of the formula IXa with a compound of the formula HX—Alk—OH (VId) or with a reactive ester, for instance a halide, such as a bromide or iodide thereof, in the manner described.

Alternatively, a nitrile of the formula IXc is reacted with a compound of the formula VId in which X represents oxygen, in the presence of an acidic condensation agent, for instance hydrogen chloride, to form the corresponding imino ester salt, which is then hydrolysed using water in an acidic medium, for example in the manner described above, to form the corresponding carboxylic acid ester.

The above reactions and also process variant (d) can be carried out under reaction conditions known per se, in the absence or customarily the presence of solvents or diluents, depending on the nature of the reaction and/or reactants at reduced elevated temperature, for example in a temperature range of from approximately $-10°$ C. to approximately 150° C., under atmospheric pressure or in a closed vessel, optionally under pressure and/or n an inert atmosphere, for example under a nitrogen atmosphere.

The groups Z present in the starting material of the formula VII of process variant (e), which can be converted by means of reduction into the group Alk, contain double and/or triple bonds and/or carbonyl or thiocarbonyl groups in the corresponding alkylene radical.

The reduction of unsaturated groups to the carbon-carbon single bond is carriedout, for example, by means of activated hydrogen, such as hydrogen in the presence of a hydrogenation catalyst, for example a nickel, platinum or palladium catalyst, whilst the reduction of carbonyl groups to the methylene group can be effected by means of hydrogen in the presence, for example, of a copper chromite catalyst or, according to Clemmensen's method, for example optionally by means of zinc amalgam in a mineral acid, for instance hydrochloric acid. If the carbonyl group to be reduced is bonded to a nitrogen atom and thus a carboxamide is present, the reduction to the methylene group can be carried out in customary manner, for example with a metal hydride, for instance lithium aluminium hydride. The reduction of thiocarbonyl groups can be carried out in a similar manner, for example using a sulphur-resistant catalyst. The reduction of the above-mentioned groups can furthermore be carried out by means of a hyride reducing agent, for example sodium borohydride or diborane. In these reductions, where desirable, care should be taken that other groups sensitive to reduction, for example unsaturated groups or nitro groups, are not attacked, and this may be achieved, for example, by selecting a suitable reducing agent, selecting the dosage thereof necessary for the reduction to be carried out and/or selecting suitable process conditions, for example elevated or reduced temperature, and/or by using a suitable solvent. These reactions are carried out in a manner known per se, customarily in the presence of solvents or diluents, depending on the nature of the reaction and/or reactants at reduced or elevated temperature, for example in a temperature range of from approximately $-15°$ C. to approximately 120° C. under normal pressure or in a closed vessel, optionally under pressure and/or under a protective gas, for instance nitrogen.

Starting materials of the formula VII can, if novel, be manufactured according to methods known per se, for example analogously to the processes described under (a) to (d). For example, it is possible to proceed analogously to the reaction steps described in stages (aa) to (ah) if there are used instead of the compounds IX, XI, XIII, XIV or XV compounds that instead of the above-defined group Va contain a group of the formula

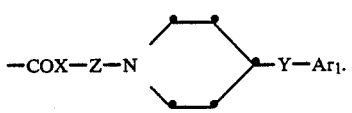
(VIIa)

For example, a starting material of the formula

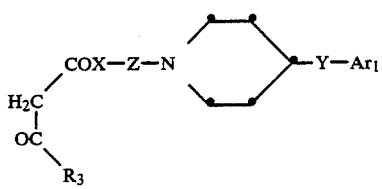
(VIIb)

can be used analogously to the methods described for the manufacture of compounds of the formula IX, for instance by reacting a compound of the formula IXa or a reactive derivative thereof, for example an anhydride, an acid halide, for instance a chloride, an azide, or a mixed ester, such as a cyanomethyl ester or a pentachlorophenol ester, with a compound of the formula IXb. Carboxylic acids of the formula IXa can also be reacted in the form of salts, especially alkali metal or alkaline earth metal salts, with reactive esters of the formula

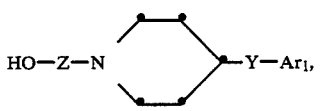
(VIIc)

such as corresponding halides, for example chlorides, bromides or iodides, or organic sulphonic acid esters, for instance those with lower alkanesulphonic acids, such as methanesulphonic acid, or arylsulphonic acids, such as benzenesulphonic acid, to form corresponding carboxylic acid esters. Alcohols of the formula VIIc may, on the other hand, be reacted with nitriles of the formula IXc in customary manner, for example in the presence of acidic condensation agents, such as a mineral acid, for instance hydrochloric or sulphuric acid, to form imino esters corresponding to the salts, which imino esters are then hydrolysed by means of water, in the manner described, to form the carboxylic acid esters. These reactions are carried out under customary reaction conditions that are known per se. Starting materials of the formula VIIc in turn can, if novel, be manufactured in customary manner, for example by reacting compounds of the formula HO—Z—A (VIId), in which A represents a suitable leaving group, for example halogen, such as chlorine, bromine or iodine, or a sulphonyloxy group, such as a p-toluenesulphonyloxy group, with compounds of the formula IXe.

Compounds of the formula I obtainable in accordance with the process can be converted in a manner known per se into other compounds of the formula I, for instance by converting substituents contained in compounds of the formula I into other substituents covered by formula I.

For example, an esterified carboxy group —COOR$_1$ can be converted into a different ester group by transesterification. There are preferably used as reagents for this alcohol compounds that have a boiling point clearly above that of the alcohol of the esterified group in the compound of the formula I to be converted, and the reaction is carried out, for example, in an excess of the alcohol compound and/or in an inert organic solvent that preferably also has a boiling point clearly above that of the alcohol of the esterified group, preferably in the presence of a catalyst, for example an alkali metal lower alkoxide, such as sodium or potassium methoxide or ethoxide, while heating and customarily with removal by distillation of the alcohol freed.

Compounds of the formula I in which Y represents the group —(C=O)— can be converted in customary manner by means of reduction into compounds of the formula I in which Y represents the group —CHOH—, it being possible for unsaturated groups that may be present to be converted into saturated groups, or groups containing triple bonds to be converted into those with double bonds.

It is possible to use for the reducton, for example, catalytically activated hydrogen, for instance hydrogen in the presence of a hydrogenation catalyst, such as a noble metal catalyst, for example platinum or palladium, or also Raney nickel. Equally, a suitable hydride reducing agent, for instance diborane or sodium borohydride, or lithium aluminium hydride, can be used in a suitable solvent, for instance one of ethereal character, such as tetrahydrofuran.

Furthermore, compounds of the formula I in which R and/or Ar$_1$ represent suitable azaheterocyclic groups of which the ring nitrogen atoms may be N-oxidised, may be converted into corresponding N-oxides. The oxidation can be carried out in a manner known per se, for example by treating with organic per acids, such as lower alkanoic per acids or arene per acids, such as optionally suitably substituted perbenzoic acids, for example peracetic or 3-chloroperbenzoic acid, preferably at room temperature or at a reaction temperature slightly above that, or with aqueous hydrogen peroxide, for example at temperatures of up to 100° C., in the presence or absence of lower alkanoic acids, for example acetic acid. Especially when using per acids, care must be taken that over-oxidation does not occur as a result of too long a reaction time.

Depending on the reaction conditions, the compounds of the formula I can be obtained in free form or in the form of salts.

Thus, resulting acid addition salts can be converted in a manner known per se, for example by treatment with a base, such as an alkali metal hydroxide, into the free compounds, or, for example, by treatment with suitable acids or derivatives thereof into other salts. Resulting free compounds of the formula I can be converted into their salts, for example by treatment with acids or corresponding anion exchangers.

Owing to the close relationship between the compounds of the formula I in free form and in the form of salts, there are to be understood hereinbefore and hereinafter by the free compounds or their salts optionally also the corresponding salts or free compounds, respectively, where appropriate with regard to meaning and purpose.

The compounds of the formula I, including the salts thereof, can also be obtained in the form of their hydrates, or their crystals may include, for example, the solvent used for crystallisation.

Depending on the chemical structure, process reaction and/or nature of the starting materials, compounds of the formula I can be obtained in the form of racemic mixtures, racemates or optical antipodes.

Resulting racemic mixtures can be separated into the pure racemates or diastereoisomers in known manner on the basis of the physico-chemical differences between the racemates, for example by chromatography and/or fractional crystallisation.

Racemates can be resolved into the optical antipodes according to methods known per se, for example by recrystallisation from an optically active solvent, with the aid of suitable microorganisms or by reaction of a compound of the formula I with salt-forming, for example basic, properties with an optically active, salt-forming agent, such as an optically active acid, and separation of the mixtures of salts obtained in this manner, for example on the basis of their different solubilities, into the diastereoisomeric salts from which the antipodes can be freed, for example by treatment with a base.

Optical antipodes of neutral compounds of the formula I can also be obtained, for example, in accordance with process (c) using an optically active acid of the formula V ($Ac^o$ represents carboxy, $Ac_1^o$ is esterified or amidated carboxy), these being obtained, for example, from the corresponding racemic acid in customary manner, for example by salt formation with an optically active base, separation of the diastereoisomeric salts and liberation of the optically active acid and conversion thereof into a compound containing the group —$COOR_1$ and corresponding to the formula I.

Also, for example, compounds of the formula I having a group —$COOR_1$ can be transesterified using an optically active alcohol in accordance with the process described above, and the resulting diastereoisomeric mixture can be separated into the antipodes, for example by means of fractional crystallisation.

Advantageously, the pharmacologically more active diastereoisomer or the more active antipode is isolated from a diastereoisomeric mixture or racemate, respectively.

The invention relates also to those embodiments of the process according to which a compound obtainable as an intermediate at any stage of the process is used as starting material and the remaining steps are carried out, or a starting material is used in the form of a derivative, for example a salt, and/or its racemate or antipode, or is formed under the reaction conditions. Salts of starting materials having salt-forming basic properties are, for example, those with mineral acids, such as hydrochloric acid, sulphuric acid or phosphoric acid, or with organic acids, for example acetic acid.

The starting materials used in the processes of the present invention are preferably those which result in the compounds described at the beginning as being especially valuable. The present invention relates also to novel starting materials and intermediates and to processes for their manufacture.

The invention relates also to the use of compounds of the formula I or pharmaceutically acceptable salts of such compounds having salt-forming properties, especially as pharmacologically active compounds, especially as coronary dilators and antihypertensives for the treatment of cardiovascular conditions, such as *Angina pectoris* and its sequelae, vascular constrictions, high blood pressure and cardiac insufficiency. They may preferably be used in the form of pharmaceutical preparations in a method for the prophylactic and/or therapeutic treatment of the animal or human body, especially for the treatment of cardiovascular conditions, such as *Angina pectoris* and its sequelae, vascular constrictions, high blood pressure and cardiac insufficiency.

The dosage of the active ingredient, which is administered on its own or together with a customary carrier and adjunct, depends on the species to be treated, the age and individual condition, and on the method of administration. For example, the daily doses for mammals with a body weight of approximately 70 kg, depending on the nature of the illness, the individual condition and age, are preferably between approximately 10 and 500 mg, especially between approximately 50 mg and approximately 250 mg, and specifically approximately from 70 mg to 150 mg in the case of oral administration.

The invention relates furthermore to pharmaceutical preparations that contain the compounds of the formula I or pharmaceutically acceptable salts of such compounds with salt-forming properties as active ingredients, to processes for their manufacture, and to the use of compounds of the formula I or the pharmaceutically acceptable salts thereof for the manufacture of medicaments in the form of coronary dilators and antihypertensives for the treatment of cardiovascular conditions, such as *Angina pectoris* and its sequelae, vascular constrictions, central and peripheral circulatory disorders, high blood pressure, arrhythmia and cardiac insufficiency,, and also for use as inhibitors of platelet aggregation.

The pharmaceutical preparations according to the invention are for enteral, such as peroral or rectal, and also for sublingual and for parenteral administration to warm-blooded animals. Corresponding dosage unit forms, especially for peroral and/or sublingual administration, for example dragées, tablets or capsules, contain preferably from approximately 10 mg to approximately 300 mg, especially from approximately 20 mg to approximately 200 mg, of a compound of the formula I, or a pharmaceutically acceptable salt of a corresponding compound capable of salt formation, together with pharmaceutically acceptable carriers.

Suitable carriers are especially fillers, such as sugars, for example lactose, saccharose, mannitol or sorbitol, cellulose preparations and/or calcium phosphates, for example tricalcium phosphate or calcium hydrogen phosphate, also binders, such as starch pastes using, for example, corn, wheat, rice or potato starch, gelatine, tragacanth, methyl cellulose and/or, if desired, disintegrators, such as the above-mentioned starches, also carboxymethyl starch, crosslinked polyvinylpyrrolidone, agar-agar, alginic acid or a salt thereof, such as sodium alginate. Adjuncts are especially flow-regulating agents and lubricants, for example silica, talc, stearic acid or salts thereof, such as magnesium or calcium stearate, and/or polyethylene glycol. Dragée cores may be provided with suitable coatings optionally resistant to gastric juices, there being used, inter alia, concentrated sugar solutions that may contain gum arabic, talc, polyvinylpyrrolidone, polyethylene glycol and/or titanium dioxide, or lacquer solutions in suitable organic solvents or solvent mixtures or, for the manufacture of coatings resistant to gastric juices, solutions of suitable cellulose preparations, such as acetylcellulose phthalate or hydroxypropylmethylcellulose phthalate. Colourings or pigments may be added to the tablets or dragée coatings, for example for identification purposes or to indicate different doses of active ingredient.

Other orally administrable pharmaceutical preparations are dry-filled capsules made of gelatine, and also soft, sealed capsules made of gelatine and a plasticiser, such as glycerin or sorbitol. The dry-filled capsules may contain the active ingredient in the form of a granulate, for example in admixture with fillers, such as lactose, binders, such as starches and/or glidants, such as talc or magnesium stearate, and optionally stabilisers. In soft capsules, the active ingredient is preferably dissolved or suspended in suitable liquids, such as fatty oils, paraffin oil or liquid polyethylene glycols, it being possible also for stabilisers to be added. Preferred are, inter alia, capsules that can be both easily bitten through, so as to achieve action that is as rapid as possible by sublingual absorption of the active ingredient, and also swallowed without being chewed.

There come into consideration as rectally administrable pharmaceutical preparations, for example suppositories that consist of a combination of the active ingredient with a suppository base. Suitable suppository bases are, for example, natural or synthetic triglycerides, paraffin hydrocarbons, polyethylene glycols or higher alkanols. It is also possible to use gelatine rectal capsules that contain a combination of the active ingredient with a base; there come into consideration as base substances, for example liquid triglycerides, polyethylene glycols and paraffin hydrocarbons.

Suitable for parenteral administration are especially aqueous solutions of an active ingredient in water-soluble form, for example a water-soluble salt, also suspensions of the active ingredient, such as corresponding oily injection suspensions, there being used suitable lipophilic solvents or vehicles, such as fatty oils, for example sesame oil, or synthetic fatty acid esters, for example ethyl oleate, or triglycerides, or aqueous injection suspensions that contain viscosity-increasing substances, for example sodium carboxymethylcellulose, sorbitol and/or dextran, and optionally stabilisers.

The pharmaceutical preparations of the present invention can be manufactured in a manner known per se, for example by means of conventional mixing, granulating, confectioning, dissolving or lyophilising processes. For example, pharmaceutical preparations for oral administration can be obtained by combining the active ingredient with solid carriers, optionally granulating a resulting mixture, and processing the mixture or granulate, if desired or necessary after the addition of suitable adjuncts, to form tablets or dragée cores.

EXAMPLE 1

Under an argon atmosphere 12.1 ml of N-ethylmorpholine and 13 g of 2-[4-(p-fluorobenzoyl)-piperidino]-ethylamine hydrochloride are added in succession to a solution of 24 g of 2,6-dimethyl-4-(3-nitrophenyl)-1,4-dihydropyrdine-3,5-dicarboxylic acid 3-(1-benzotriazoly)-ester 5-methyl ester in 60 ml of dimethylformamide and the suspension is stirred for 1 hour while cooling with ice, then for 1 hour at 20° and finally for 17 hours at a bath temperature of 60°. The reaction mixture is then freed of solvent in a rotary evaporator under a high vacuum and the residue is dissolved in 150 ml of ethyl acetate and 50 ml of water. The organic phase is dried over sodium sulphate and concentrated by evaporation and the resulting crude product is chromatographed over 1 kg of silica gel using methylene chloride/methanol (95:5) in order to remove impurities and then using a methylene chloride/methanol mixture (9:1) in order to elute the desired product. After removal of the solvent the resulting product is dissolved in ethyl acetate and converted into the hydrochloride with 30 ml of 2N hydrochloric acid; the hydrochloride is filtered with suction and washed with water and ethyl acetate. After recrystallisation from 60 ml of an ethanol/water mixture 1:1 there is obtained 2,6-dimethyl-4-(3-nitrophenyl)-1,4-dihydropyridine-3-carboxylic acid methyl ester 5-N-[2-[4-(p-fluorobenzoyl)-piperidino]ethyl]-carboxamide hydrochloride which decomposes from 200°.

The starting material can be manufactured as follows:

A solution of 2,6-dimethyl-4-(3-nitrophenyl)-1,4-dihydropyridine-3,5-dicarboxylic acid monomethyl ester [European patent application No. 11 706], 3.4 g of 1-hydroxybenzotriazole and 4.6 g of N,N'-dicyclohexyl carbodiimide in 100 ml of anhydrous dimethylformamide is left to stand at 0°–5° for 16 hours under a nitrogen atmosphere. The N,N'-dicyclohexylurea that crystallises out is filtered off. 300 ml of water are added to the yellow filtrate while cooling with an ice bath and the whole is stirred for 1 hour at 0°–5°, the amorphous crude product being deposited. The crude product is filtered off and the filtration residue is washed with 400 ml of water and dried in vacuo. For further purification the crude product is dissolved in 40 ml of ethyl acetate and stirred at 0°–5° for 1 hour. The N,N'-dicyclohexylurea that crystallises out is then removed by filtration and the filtrate is concentrated by evaporation under reduced pressure, yielding 2,6-dimethyl-4-(3-nitrophenyl)-1,4-dihydropyridine-3,5-dicarboxylic acid 3-(1-benzotriazoly)ester 5-methyl ester in the form of a highly viscous foam.

EXAMPLE 2

A mixture of 11.9 g of 2,6-dimethyl-4-(3-nitrophenyl)-1,4-dihydropyridine-3,5-dicarboxylic acid methyl ester 2-chloroethyl ester (DOS 2 407 115), 7.3 g of 4-(p-fluorobenzoyl)-piperidine hydrochloride, 11.4 ml of N-ethyl-N,N-diisopropylamine and 60 ml of xylene is stirred under an argon atmosphere at a bath temperature of 150° for 8 hours. The solvent is then removed in a rotary evaporator in vacuo, yielding 30 g of a brown oil which is taken up in 150 ml of ethyl acetate and 50 ml of water. After the organic phase has been separated off it is washed with water and saturated aqueous sodium chloride solution and then dried over sodium sulphate. After evaporation to dryness there remain 20 g of an oil which is chromatographed over 700 g of silica gel Merck 9385 (0.04–0.063 mm) with a hexane/ethyl acetate mixture 1:1. The eluted product is dissolved in ether, and 3N ethereal hydrogen chloride solution is added dropwise to the solution, yielding 2,6-dimethyl-4-(3-nitrophenyl)-1,4-dihydropyridine-3,5-dicarboxylic acid methyl ester 2-[4-(p-fluorobenzoyl)-piperidino]-ethyl ester hydrochloride which melts from 136° with decomposition.

EXAMPLE 3

A mixture of 18.2 g of 2,6-dimethyl-4-(3-nitrophenyl)-1,4-dihydropyridine-3,5-dicarboxylic acid methyl ester 6-chloro-n-hexyl ester and 16.6 g of 4-(p-fluorobenzoyl)-piperidine is stirred with a spatula in a bath heated to 140° until it melts and heated at 140° for 1 hour. The reaction mass is scraped out of the flask and stirred with a mixture of 250 ml of ethyl acetate, 350 ml of methylene chloride and 100 ml of 50% aqueous potassium carbonate solution. The organic phase is washed with aqueous potassium carbonate solution, dried over potassium carbonate, filtered and concentrated by evaporation. The residue is chromatographed over 700 g of silica gel, hexane/ethyl acetate/methanol (4:4:0.5) being used as eluant. There is thus obtained 2,6-dimethyl-4-(3-nitrophenyl)-1,4-dihydropyridine-3,5-dicarboxylic acid methyl ester 6-[4-(p-fluorobenzoyl)-piperidino]-n-hexyl ester which is converted by means of ethereal hydrogen chloride solution into the amorphous hydrochloride which melts from 45°.

The 2,6-dimethyl-4-(3-nitrophenyl)-1,4-dihydropyridine-3,5-dicarboxylic acid methyl ester 6-chloro-n-hexyl ester used as starting material can be manufactured analogously to the procedure described in Example 11 of DOS 2 407 115 using acetoacetic acid 6-chloro-n-hexyl ester, and is further processed as a crude product.

EXAMPLE 4

A mixture of 16.4 g of 2,6-dimethyl-4-(3-nitrophenyl)-1,4-dihydropyridine-3,5-dicarboxylic acid methyl ester 3-chloropropyl ester and 16.6 g of 4-(p-fluorobenzoyl)-piperidine is kept for 1 hour under argon in a bath heated to 145°. After cooling, 100 ml of ethyl acetate and 50 ml of 2N hydrochloric acid are added and the mixture is stirred until the reaction mass has completely dissolved. The partly oily aqueous-acidic phase is adjusted to pH 10 with 50% potassium carbonate solution; methylene chloride is added and the whole is filtered with suction. The methylene chloride phase of the filtrate is separated off and concentrated by evaporation and the residue is dissolved in ethyl acetate; the solution is dried over sodium sulphate and filtered. Filtration is then carried out over 1 kg of silica gel Merck 9385 using a hexane/ethyl acetate/methanol mixture (4:2:0.5) as eluant. The 2,6-dimethyl-4-(3-nitrophenyl)-1,4-dihydropyridine-3,5-dicarboxylic acid methyl ester 3-[4-(p-fluorobenzoyl)-piperidino]-propyl ester obtained after working up is converted by means of ethereal hydrogen chloride solution into the hydrochloride which, after recrystallisation from isopropanol, melts at 198°–205° with the evolution of gas.

The 2,6-dimethyl-4-(3-nitrophenyl)-1,4-dihydropyridine-3,5-dicarboxylic acid methyl ester 3-chloropropyl ester used as starting material can be manufactured analogously to the procedure described in Example 11 of DOS 2 407 115 using acetoacetic acid 3-chloropropyl ester, and is further processed as the crude product.

EXAMPLE 5

A mixture of 11 g of 2,6-dimethyl-4-(3-nitrophenyl)-1,4-dihydropyridine-3,5-dicarboxylic acid methyl ester 2-chloroethyl ester, 6.4 g of 4-(2-thenoyl)-piperidine and 8.8 ml of 1,8-diazabicyclo[5.4.0]undec-7-ene is stirred under argon for 1 hour in a bath at 150°. After cooling, the melt is dissolved in 100 ml of ethyl acetate and the solution is washed three times with 1N hydrochloric acid. The aqueous-acidic solution is adjusted to pH 9–10 with 50% potassium carbonate solution and extracted with ethyl acetate. The organic phase is dried over sodium sulphate and concentrated by evaporation and the residue is dissolved in ether. By the addition of a solution of hydrogen chloride in ether there is obtained 2,6-dimethyl-4-(3-nitrophenyl)-1,4-dihydropyridine-3,5-dicarboxylic acid methyl ester 2-[4-(2-thenoyl)-piperidino]-ethyl ester hydrochloride which melts at 140°–145°; it sinters from 120°.

EXAMPLE 6

A mixture of 8.4 g of 2,6-dimethyl-4-(2,3-dichlorophenyl)-1,4-dihydropyridine-3,5-dicarboxylic acid methyl ester 2-chloroethyl ester and 8.8 g of 4-(p-fluorobenzoyl)-piperidine is stirred under argon for 1 hour at a temperature of 145°. After working up, the resulting residue is chromatographed over 500 g of silica gel, yielding 2,6-dimethyl-4-(2,3-dichlorophenyl)-1,4-dihydropyridine-3,5-dicarboxylic acid methyl ester 2-[4-(p-fluorobenzoyl)-piperidino]-ethyl ester in amorphous form which exhibits the following characteristic bands in th NMR spectrum: $^1$H-NMR (CDCl$_3$): 2.3 and 2.4 [2S, 6H, 2 H$_3$C—C (2 and 6)]; 3.6 [s, 3H, H$_3$C—OOC]; 5.4 [s, 1H, H-c (4)], 7.1–8.1 (m, 7H, 7 arom. H). R$_f$ value: 0.40 (hexane/ethyl acetate/methanol=4:2:1).

The 2,6-dimethyl-4-(2,3-dichlorophenyl)-1,4-dihydropyridine-3,5-dicarboxylic acid methyl ester 2-chloroethyl ester used as starting material can be obtained analogously to the procedure described in Example 11 of DOS 2 407 115 using 2,3-dichlorobenzaldehyde, and is further processed as a crude product.

EXAMPLE 7

A mixture of 4.4 g of 4-(p-fluorobenzoyl)piperidine and 4.1 g of 2,6-dimethyl-4-(2,1,3-benzoxadiazol-4-yl)-1,4-dihydropyridine-3,5-dicarboxylic acid methyl ester 3-chloropropyl ester is reacted analogously to the procedure described in Example 6. The residue obtained after chromatography over silica gel is 2,6-dimethyl-4-(2,1,3-benzoxadiazol-4-yl)-1,4-dihydropyridine-3,5-dicarboxylic acid methyl ester 3-[4-(p-fluorobenzoyl)-piperidino]-propyl ester which exhibits the following characteristic bands in the NMR spectrum: $^1$H-NMR (CDCl$_3$): 2.4 (2s, 6H, 2 H$_3$C—C (2 and 6); 3.6 (s, 3H, H$_3$C—OOC); 4.1 (t, 2H, H$_3$C—OOC); 5.4 [s, 1H, H—C (4)]; 7.2–8.1 (m, 7H, 7 arom. H); R$_f$ value: 0.27 (hexane/ethyl acetate/methanol=4:2:1).

The 2,6-dimethyl-4-(2,1,3-benzoxadiazol-4-yl)-1,4-dihydropyridine-3,5-dicarboxyic acid methyl ester chloropropyl ester required as starting material can be obtained analogously to the procedure described in Example 11 of DOS 2 407 115 using 3-chloropropyl acetoacetate, 2,1,3-benzoxadiazole-4-carboxaldehyde and methyl-β-aminocrotonate, and is further processed as a crude product.

EXAMPLE 8

To a mixture of 12 ml of dimethylformamide and 7,3 ml of acetonitrile a solution of 0,86 ml of oxalylchloride in 4,7 ml of acetonitrile is added dropwisely at −20° to −15°. After 15 minutes at the same temperature 3,3 g of (+)−2,6-dimethyl-4-(3-nitrophenyl)-1,4-dihydropyridine-3,5-dicarboxylic acid monomethyl ester are added and the yellow suspension is allowed to reach 0° and is kept for 30 minutes. The resulting yellow solution is then cooled to −20°. To this solution a solution of 2,9 g of 2-[4-(p-fluorobenzoyl)piperidino]ethanol in 10 ml of acetonitrile and 10 ml of pyridine is added dropwise. The yellow suspension is allowed to stand over night at room temperature and is then added to a mixture of 50 ml of 2N sodium hydroxide and 100 g of ice and the resulting solution is decanted from the precipitate formed. The precipitate is dissolved in 40 ml of ethyl acetate and washed with 60 ml of 1N hydrochloric acid, with water and with a saturated solution of potassium hydrogen-carbonate. After drying and evaporating to dryness a yellow resin is obtained. It is purified using silica gel (Merck 9385) with hexane/ethyl acetate. The eluted product is dissolved in 50 ml of ether, filtered off and allowed to stand for 15 hours. The resulting yellow powder is dissolved in 60 ml of tert. butyl methyl ether. To this solution 2,3 ml of 3N hydrochloric acid in ether is added dropwise. To facilitate stirring additional 100 ml of tert-butyl methyl ether are added. After filtration and drying the hydrochloride of (−)−(4R)-2,6-dimethyl-4-(3-nitrophenyl)-1,4-dihydropyridine-3,5-dicarboxylic acid 2-[4-(4-fluorobenzoyl)-1-piperidinyl]ethyl ester methyl ester is obtained after recrystallization from acetonitrile, mp. 211°–213° (dec.); $[\alpha]_D$: −83,6±1,0° (methanol).

The starting material can be manufactured as follows: 29,4 g of cinchonidine and 33,2 g of racemic 2,6-dimethyl-4-(3-nitrophenyl)-1,4-dihydropyridine-3,5-dicarboxylic acid monomethyl ester [European Patent Application No. 11,706, Example 1, Table 1] are dissolved in 3 l of refluxing acetonitrile and the yellow solution is allowed to cool slowly to room temperature. After standing for two days, the resulting crystals are filtered off, washed with acetonitrile and recrystallized from 1300 ml of acetonitrile yielding the slightly yellow cinchonidine salt, m.p. 186°–187° (dec.). This salt is treated with 1 l of ethyl acetate and 200 ml of 1N hydrochloric acid. The aqueous solution is extracted with ethyl acetate and the organic phase is dried over sodium sulphate and evaporated to dryness.

The remaining crystals are washed with 50 ml of ether and dried. There is thus obtained (+)−2,6-dimethyl-4-(3-nitrophenyl)-1,4-dihydropyridine-3,5-dicarboxylic ester monomethyl ester, m.p. 187°–188° (dec.); $[\alpha]_D$: +22,6±1,7 (acetone].

The mother liquor from the above procedure (3,2 l of acetonitrile solution) is concentrated to about 1,6 l by evaporation whereupon 2,5 g of cinchonidine are recovered. After further concentration of the filtrate to about 0,8 l and keeping at room temperature there are obtained crystals. Recrystallization from acetonitrile yields the cinchonidine salt (m.p. 147°–148°, dec.). The free acid of (−)−2,6-dimethyl-4-(3-nitrophenyl)-1,4-dihydro-pyridine-3,5-dicarboxylic acid monomethyl ester can be obtained as described above. (−)−2,6-dimethyl-4-(3-nitrophenyl)-1,4-dihydropyridine-3,5-dicarboxylic acid monomethyl ester melts at 182°–183° (dec.); $[\alpha]_D$: −22,3±1,8 (acetone).

EXAMPLE 9

In a manner analogously to the procedure described in Example 8 (+)−(4S)-2,6-dimethyl-4-(3-nitrophenyl)-1,4-dihydropyridine-3,5-dicarboxylic acid 2-[4-(4-fluorobenzoyl)-1-piperidinyl]ethyl ester methyl ester is obtained, m.p. 212°–214° (dec.); $[\alpha]_D$: +86,4±1,0 (methanol), starting from (−)-2,6-dimethyl-4-(3-nitrophenyl)-1,4-dihydropyridine-3,5-dicarboxylic acid monomethyl ester and 2-[4-(p-fluorobenzoyl)-piperidino]ethanol.

EXAMPLE 10

Tablets containing 20 mg of active ingredient are manufactured in customary manner with the following composition:

Composition

| | |
|---|---|
| 2,6-dimethyl-4-(3-nitrophenyl)-1,4-dihydro-pyridine-3-carboxylic acid methyl ester 5-N—[2-[4-(p-fluorobenzoyl)-piperidino]-ethyl]-carboxamide | 20 mg |
| wheat starch | 60 mg |
| lactose | 50 mg |
| colloidal silica | 5 mg |
| talc | 9 mg |
| magnesium stearate | 1 mg |
| | 145 mg |

Manufacture

The active ingredient is mixed with a portion of the wheat starch, with the lactose and colloidal silica and the mixture is forced through a sieve. A further portion of the wheat starch is made into a paste with 5 times the amount of water on a water bath and the pulverulent mixture is kneaded with this paste until a slightly plastic mass has formed.

The plastic mass is pressed through a sieve of approximately 3 mm mesh width and dried, and the resulting dry granulate is again forced through a sieve. The remainder of the wheat starch, the talc and magnesium stearate are then mixed in and the mixture is compressed to form tablets weighing 145 mg and having a breaking groove.

EXAMPLE 11

Tablets containing 1 mg of active ingredient are manufactured in customary manner with the following composition:

Composition

| | |
|---|---|
| 2,6-dimethyl-4-(3-nitrophenyl)-1,4-dihydro-pyridine-3,5-dicarboxylic acid methyl ester 2-[4-(p-fluorobenzoyl)-piperidinol-ethyl ester | 1 mg |
| wheat starch | 60 mg |
| lactose | 50 mg |
| colloidal silica | 5 mg |
| talc | 9 mg |
| magnesium stearate | 1 mg |
| | 126 mg |

Manufacture

The active ingredient is mixed with a portion of the wheat starch, with the lactose and colloidal silica and the mixture is forced through a sieve. A further portion of the wheat starch is made into a paste with 5 times the amount of water on a water bath and the pulverulent mixture is kneaded with this paste until a slightly platic mass has formed.

The plastic mass is pressed through a sieve of approximately 3 mm mesh width and dried, and the resulting dry granulate is again forced through a sieve. The remainder of the wheat starch, the talc and magnesium stearate are then mixed in and the mixture is compressed to form tablets weighing 126 mg and having a breaking notch.

EXAMPLE 12

Capsules containing 10 mg of active ingredient are manufactured in customary manner as follows:

Composition

| | |
|---|---|
| 2,6-dimethyl-4-(3-nitrophenyl)-1,4-dihydropyridine-3-carboxylic acid methyl ester 5-N-[2-[4-(p-fluorobenzoyl)-piperidino]-ethyl]-carboxamide | 2500 mg |
| talc | 200 mg |
| colloidal silica | 50 mg |

Manufacture:

The active ingredient is intimately mixed with the talc and colloidal silica, the mixture is forced through a sieve of 0.5 mm mesh width and introduced in 11 mg portions into hard gelatine capsules of suitable size.

EXAMPLE 13

Instead of the compounds used as active ingredient in Examples 10 to 12 it is also possible to use the following compounds of the formula I or their pharmaceutically acceptable, non-toxic acid addition salts as active ingredients in tablets, dragées, capsules, etc.:

2,6-dimethyl-4-(3-nitrophenyl)-1,4-dihydropyridine-3,5-dicarboxylic acid methyl ester 6-[4-(p-fluorobenzoyl)piperidino]-n-hexyl ester, 2,6-dimethyl-4-(3-nitrophenyl)-1,4-dihydropyridine-3,5-dicarboxylic acid methyl ester 3-[4-(p-fluorobenzoyl)piperidino]-propyl ester, 2,6-dimethyl-4-(3-nitrophenyl)-1,4-dihydropyridine-3,5-dicarboxylic acid methyl ester 2-[4-(2-thenoyl)-piperidino]-ethyl ester, 2,6-dimethyl-4-(2,3-dichlorophenyl)-1,4-dihydropyridine-3,5-dicarboxylic acid methyl ester 2-[4-(p-fluorobenzoyl)-piperidino]-ethyl ester, 2,6-dimethyl-4-(2,1,3-benzoxadiazol-4-yl)-1,4-dihydropyridine-3,5-dicarboxylic acid methyl ester [4-(p-fluorobenzoyl)-piperidino]-propyl ester, (−)-(4R)- and (+)-(4S)-2,6-dimethyl-4-(3-nitrophenyl)-1,4-dihydropyridine-3,5-dicarboxylic ester monomethyl ester.

I claim:

1. A compound of formula I

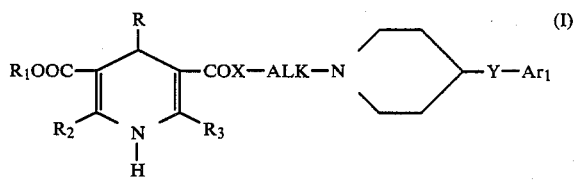

wherein
R is phenyl which is mono or disubstituted by lower alkyl, lower alkoxy, halogen-lower alkoxy, halogen-lower alkenyloxy or halogen, wherein said halogen group has an atomic number 35 or less, or mono substituted by $CF_3$, $NO_2$, or $CN$, said phenyl substituents occupying the 2- or 3-position of said phenyl ring;
$R_1$, $R_2$, and $R_3$ each represents lower alkyl
X is oxygen or —NH—;
Alk is —$(CH_2)_n$— wherein n is 2-6;
Y is carbonyl; and
$Ar_1$ is phenyl which is substituted by halogen of atomic number 35 or less; or a pharmaceutically acceptable salt thereof.

2. A compound of formula I

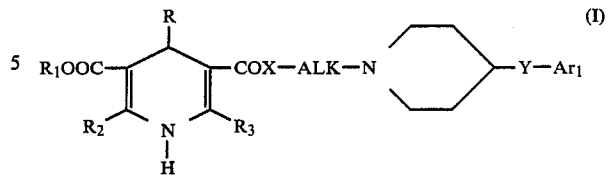

wherein
R is phenyl which is mono or disubstituted by halogen having an atomic number 35 or less, or mono substituted by $CF_3$, $NO_2$, or $CN$, said phenyl substituents occupying the 2- or 3-position of said phenyl ring;
$R_1$, $R_2$, and $R_3$ each represents lower alkyl
X is oxygen; and
Alk is —$(CH_2)_n$— wherein n is 2 or 3;
Y is carbonyl; and
$Ar_1$ is phenyl which is substituted by halogen of atomic number or less; or a pharmaceutically acceptable salt thereof.

3. A compound of claim 2 wherein
R is phenyl which is mono or di substituted by halogen of atomic number 35 or less, or mono substituted by nitro, said phenyl substituent accupying the 2- or 3-position of said phenyl ring; or a pharmacetically acceptable salt thereof.

4. A compound of claim 3 wherein
$R_1$ is methyl or ethyl;
$R_2$ and $R_3$ are each methyl; and
$Ar_1$, is phenyl substituted in the 4-position by halogen of atomic number 35 or less; or a pharmaceutically acceptable salt thereof.

5. A compound selected from the group consisting of 2,6-dimethyl-4-(3-nitrophenyl)-1,4-dihydropyridine-3-carboxylic acid methyl ester-5-N-[2-[4-(p-fluorobenzoyl)-piperidinol]ethyl]carboxamide; 2,6-dimethyl-4-(3-nitrophenyl)-1,4-dihydropyridine-3,5-dicarboxylic acid methyl ester-2-[4-(p-fluorobenzoyl)piperidino-ethyl]-ester; 2,6-dimethyl-4-(3-nitrophenyl)-1,4-dihydropyridine-3,5-dicarboxylic acid methyl ester-6-[4-(p-fluorobenzoyl)-piperidino]-n-hexyl ester; 2,6-dimethyl-4-(3-nitrophenyl)-1,4-dihydropyridine-3,5-dicarboxylic acid methyl ester-3-[4-(p-fluorobenzoyl)-piperidino]-propyl ester; and 2,6-dimethyl-4-(2,3-dichlorophenyl)-1,4-dihydropyridine-3,5-dicarboxylic acid methyl ester-2-[4-(p-fluorobenzoyl)-piperidino]-ethyl ester; or a pharmaceutically acceptable salt thereof.

6. 2,6-dimethyl-4-(3-nitrophenyl)-1,4-dihydropyridine-3-carboxylic acid methyl ester-5-N-[2-[4-(p-fluorobenzoyl)-piperidino]-ethyl]-carboxamide of claim 5 or a phrmaceutically acceptable salts thereof.

7. 2,6-dimethyl-4-(3-nitrophenyl)-1,4-dihydropyridine-3,5-dicarboxylic acid methyl ester-2-[4-(p-fluorobenzoyl)-piperidino]-ethyl ester of claim 5 and pharmaceutically acceptable saltsthereof.

8. 2,6-dimethyl-4-(3-nitrophenyl)-1,4-dihydropyridine-3,5-dicarboxylic acid methyl ester-6-[4-(p-fluorobenzoyl)-piperidino]-n-hexyl ester of claim 5 or a salt thereof.

9. 2,6-dimethyl-4-(3-nitrophenyl)-1,4-dihydropyridine-3,5-dicarboxylic acid methyl ester-3-[4-(p-fluorobenzoyl)-piperidino]-propyl ester of claim 5 and pharmaceutically acceptabe salts thereof.

10. 2,6-dimethyl-4-(2,3-dichlorophenyl)-1,4-dihydropyridine-3,5-dicarboxylic acid methyl ester-2-[4-(p- fluorobenzoyl)-piperidino]-ethyl ester of claim 5 and pharmaceutically acceptable salts thereof.

11. An optical isomer of a compound of claim 5.

12. An optical isomer of the compound of claim 7.

13. A compound according to claim 5 being 2,6-dimethyl-4-(3-nitrophenyl)-1,4-dihydropyridine-3,5-dicarboxy lic acid methyl ester-2-[4-(p-fluorobenzoyl)-piperdino-ethyl]ester.

14. A compound according to claim 5 being 2,6-dimethyl-4-(2,3-dichlorophenyl)-1,4-dihydropyridine-3,5-dicarboxylic acid methyl ester-2-[4-(p-fluorobenzoyl)piperidinol]-ethyl ester.

15. A compound according to claim 7 being (−)-(4R)-2,6-dimethyl-4-(3-nitrophenyl)-1,4-dihydropyridine-3,5-dicarboxylic acid 2-[4-(4-fluorobenzoyl)-1-piperidinyl]ethyl ester methyl ester.

16. A compound according to claim 12 being (+)-(4S)-2,6-dimethyl-4-(3-nitrophenyl)-1,4-dihydropyridine-3,5-dicarboxylic acid 2-[4-(4-fluorobenzoyl)-1-piperidinyl]ethyl ester methyl ester.

17. An optical isomer of a compound of claim 1.

18. A pharmaceutical composition useful as calcium-antagonist, α-receptor blocker and serotonin-antagonist, anti-hypertensor and coronary dilator for the treatment of Angina pectoris and its sequelae, vascular constrictions, central and peripheral circulatory disorders, high blood pressure, arrythmia and cardiac insufficiency and for the inhibition of platelet aggregation comprising a therapeutically effective amount of a compound of the formula I as claimed in claim 1, or a pharmaceutically acceptable non-toxic acid addition salt of such compound together with a pharmaceutically acceptable excipient.

19. A method for the treatment of Angina pectoris and its sequelae, vascular constrictions, central and peripheral circulatory disorders, high blood pressure, arrythmia and cardiac insufficiency and for the inhibition of platelet aggregation in a warm-blooded animal which comprises the administration thereto of a therapeutically effective amount of a compound of the formula I as claimed in claim 1, or a pharmaceutically acceptable non-toxic acid addition salt of such compound.

20. 2,6-dimethyl-4-(3-nitrophenyl)-1,4-dihydropyridine-3,5-dicarboyxlic acid methyl ester-2-[4-(2-theonyl)-piperidino]-ethyl ester of a pharmaceutically salt thereof.

21. 2,6-dimethyl-4-(3-nitrophenyl)-1,4-dihydropyridine-3,5-dicarboxylic acid methyl ester-2-[4-(2-theonyl)piperidino]-ethyl ester.

* * * * *